(12) United States Patent
Maeda et al.

(10) Patent No.: US 8,260,016 B2
(45) Date of Patent: Sep. 4, 2012

(54) IMAGE PROCESSING SYSTEM, IMAGE PROCESSING METHOD, AND COMPUTER READABLE MEDIUM

(75) Inventors: Kiyohiro Maeda, Kanagawa (JP); Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 925 days.

(21) Appl. No.: 12/331,785

(22) Filed: Dec. 10, 2008

(65) Prior Publication Data

US 2009/0147999 A1    Jun. 11, 2009

(30) Foreign Application Priority Data

Dec. 10, 2007   (JP) ................................. 2007-318616

(51) Int. Cl.
*G06K 9/00* (2006.01)
(52) U.S. Cl. .......... 382/128; 128/922; 604/6.08; 607/22
(58) Field of Classification Search .................. 382/100, 382/128–134; 128/922; 378/4–27; 604/6.08; 607/22, 88, 94, 95, 100
See application file for complete search history.

(56) References Cited

U.S. PATENT DOCUMENTS

| | | | |
|---|---|---|---|
| 7,647,085 B2 * | 1/2010 | Cane et al. ................... | 600/410 |
| 2001/0056237 A1 * | 12/2001 | Cane et al. ................... | 600/475 |
| 2004/0260165 A1 * | 12/2004 | Cho et al. ................... | 600/365 |
| 2005/0059868 A1 * | 3/2005 | Schurman ................... | 600/323 |
| 2006/0264719 A1 * | 11/2006 | Schurman et al. ............ | 600/316 |
| 2008/0021293 A1 * | 1/2008 | Schurman et al. ............ | 600/316 |

FOREIGN PATENT DOCUMENTS

| | | |
|---|---|---|
| EP | 1 302 152 A1 | 4/2003 |
| JP | 2003-505115 T | 2/2003 |
| JP | 2004-230000 A | 8/2004 |
| WO | 00/32099 A1 | 6/2000 |
| WO | 01/03571 A1 | 1/2001 |
| WO | 2006/062895 A2 | 6/2006 |

OTHER PUBLICATIONS

EP Communication, dated Apr. 3, 2009, issued in corresponding EP Application No. 08021396.0, 6 pages.

* cited by examiner

*Primary Examiner* — Anand Bhatnagar
(74) *Attorney, Agent, or Firm* — Sughrue Mion, PLLC

(57) ABSTRACT

Provided is an image processing system, including a depth calculating section that calculates a depth of an object from a surface of a body, the object existing inside the body; a light receiving section that receives light from the object; and a substance amount calculating section that calculates an amount of a substance, which generates the light received by the light receiving section, inside the object based on the depth of the object calculated by the depth calculating section and an amount of light received by the light receiving section.

18 Claims, 13 Drawing Sheets

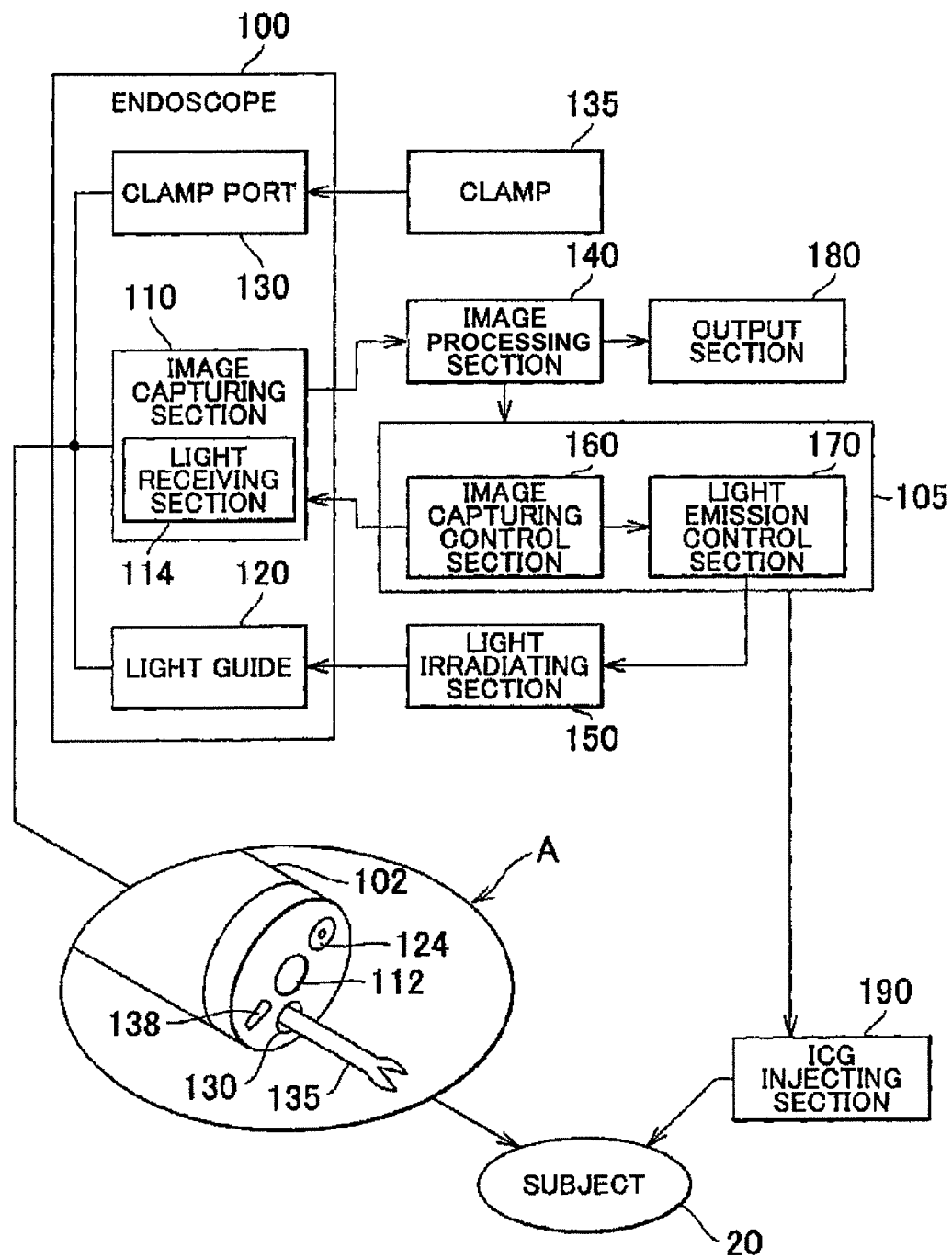
F I G . 1

| IR | R | G | B | ICG CONCENTRATION | DEPTH |
|---|---|---|---|---|---|
| $I_{IR}$ | $I_R$ | $I_G$ | $I_B$ | $C_{ICG}$ | $D_a$ |
| ... | ... | ... | ... | ... | ... |

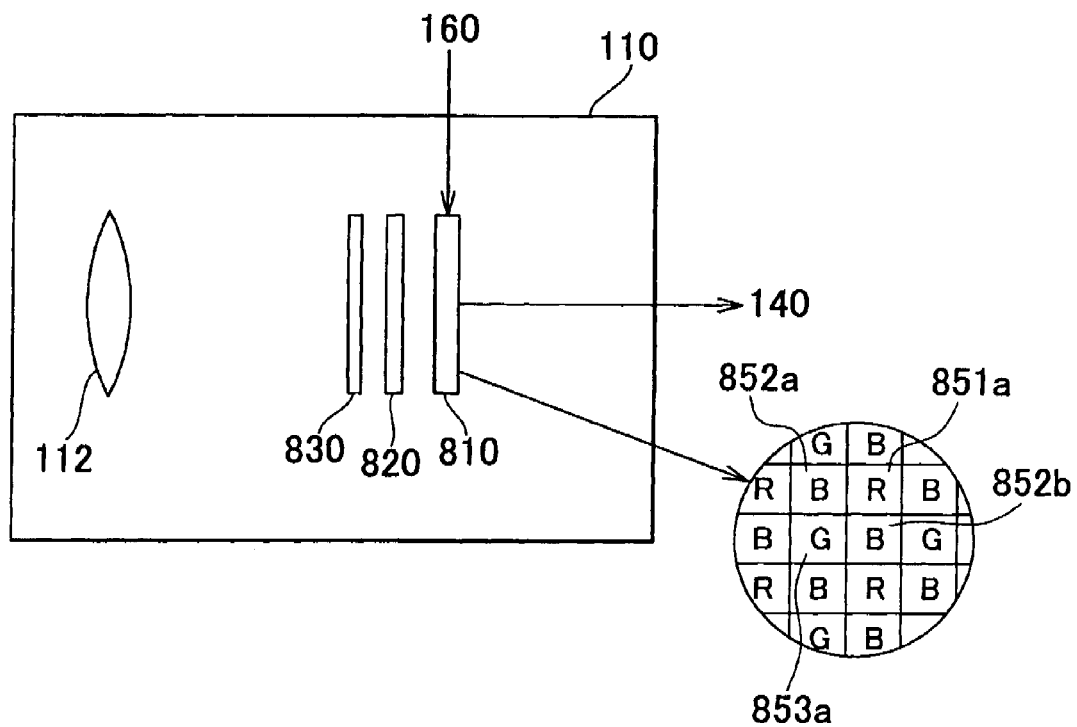
F I G. 8
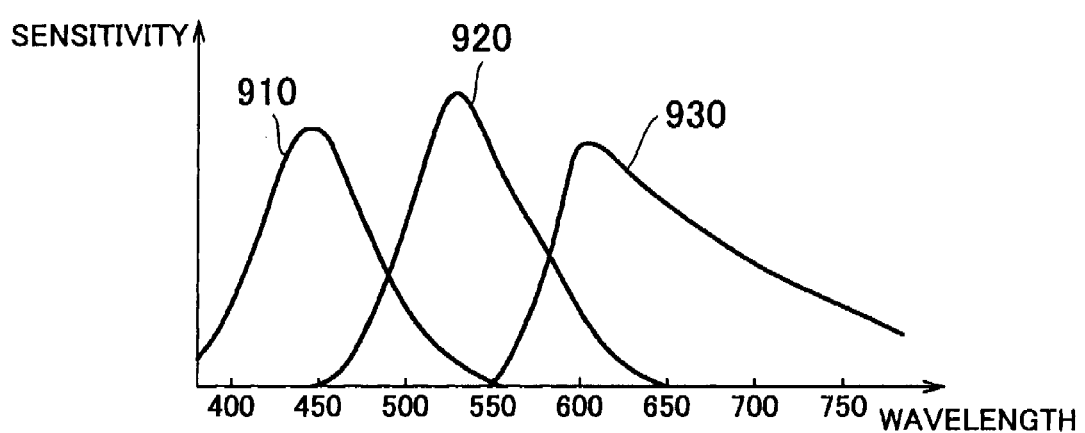
F I G. 9

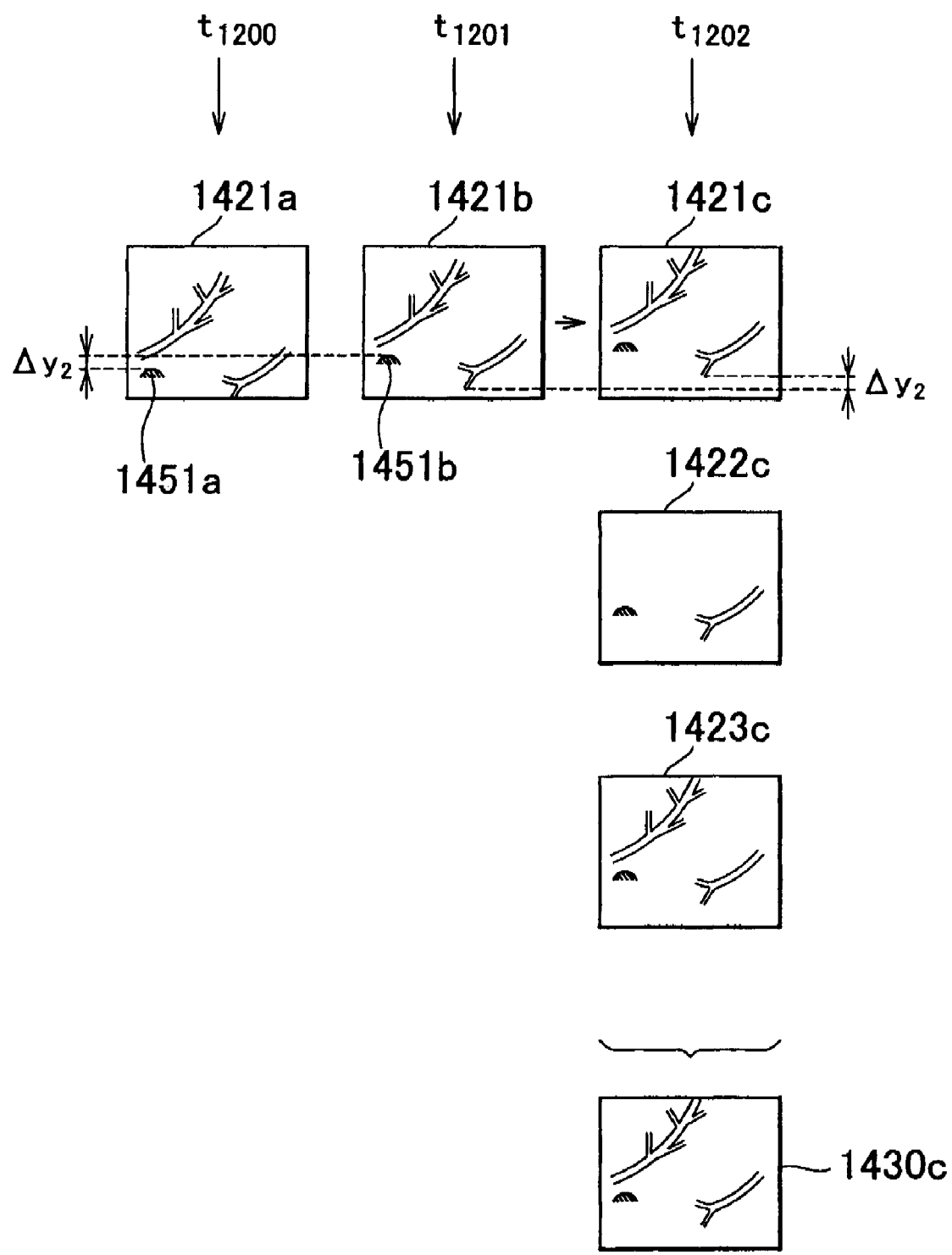
F I G. 14

IMAGE PROCESSING SYSTEM, IMAGE PROCESSING METHOD, AND COMPUTER READABLE MEDIUM

CROSS REFERENCE TO RELATED APPLICATION

The present application claims priority from a Japanese Patent Application No. 2007-318616 filed on Dec. 10, 2007, the contents of which are incorporated herein by reference.

BACKGROUND

1. Technical Field

The present invention relates to an image processing system, an image processing method, and a computer readable medium. In particular, the present invention relates to an image processing system, an image processing method, and a program used by the image processing system for calculating the amount of a substance inside an object.

2. Related Art

An apparatus for measuring an amount of a light absorbing substance in blood based on pulse photometry is known as in, for example, Japanese Patent Application Publication 2004-230000. A digital oximeter that non-invasively measures oxygen saturation in an artery is known as in, for example, Japanese Unexamined Patent Application Publication No. 2003-505115.

The light from blood inside an organism is absorbed or scattered by a substance depending on the depth of the blood. The spectral intensity of the blood changes depending on the concentration of the absorptive component or the light emitting component, such as indo-cyanine green, in the blood. Therefore, the substance concentrations calculated by the apparatuses described above include a significant error resulting from the depth and concentration of the indo-cyanine green, or the like.

SUMMARY

Therefore, it is an object of an aspect of the innovations herein to provide a an image processing system, an image processing method, and a computer readable medium, which are capable of overcoming the above drawbacks accompanying the related art. The above and other objects can be achieved by combinations described in the independent claims. The dependent claims define further advantageous and exemplary combinations of the innovations herein.

According to a first aspect related to the innovations herein, one exemplary image processing system may include a depth calculating section that calculates a depth of a first object from a surface of a body, the first object existing inside the body; a light receiving section that receives light from the first object; and a substance amount calculating section that calculates an amount of a substance, which generates the light received by the light receiving section, inside the first object based on the depth of the first object calculated by the depth calculating section and an amount of light received by the light receiving section.

According to a second aspect related to the innovations herein, one exemplary image processing method may include calculating a depth of a first object from a surface of a body, the first object existing inside the body; receiving light from the first object; and calculating an amount of a substance, which generates the received light, inside the first object based on the calculated depth of the first object and an amount of received light.

According to a third aspect related to the innovations herein, one exemplary computer readable medium may store thereon a program for use with an image processing system, when executed the program causing the image processing system to function as a depth calculating section that calculates a depth of a first object from a surface of a body, the first object existing inside the body; a light receiving section that receives light from the first object; and a substance amount calculating section that calculates an amount of a substance, which generates the light received by the light receiving section, inside the first object based on the depth of the first object calculated by the depth calculating section and an amount of light received by the light receiving section.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 shows an exemplary configuration of an image processing system 10 according to the present embodiment, along with a subject 20.

FIG. 5 is a table showing exemplary data stored in the depth information storing section 232.

FIG. 8 shows an exemplary configuration of the image capturing section 110.

FIG. 9 shows exemplary spectral sensitivity characteristics of the first light receiving element 851, the second light receiving element 852, and the third light receiving element 853.

FIG. 14 shows another example of the generation of a subject image in which the movement is corrected.

DESCRIPTION OF EXEMPLARY EMBODIMENTS

Figure 2:
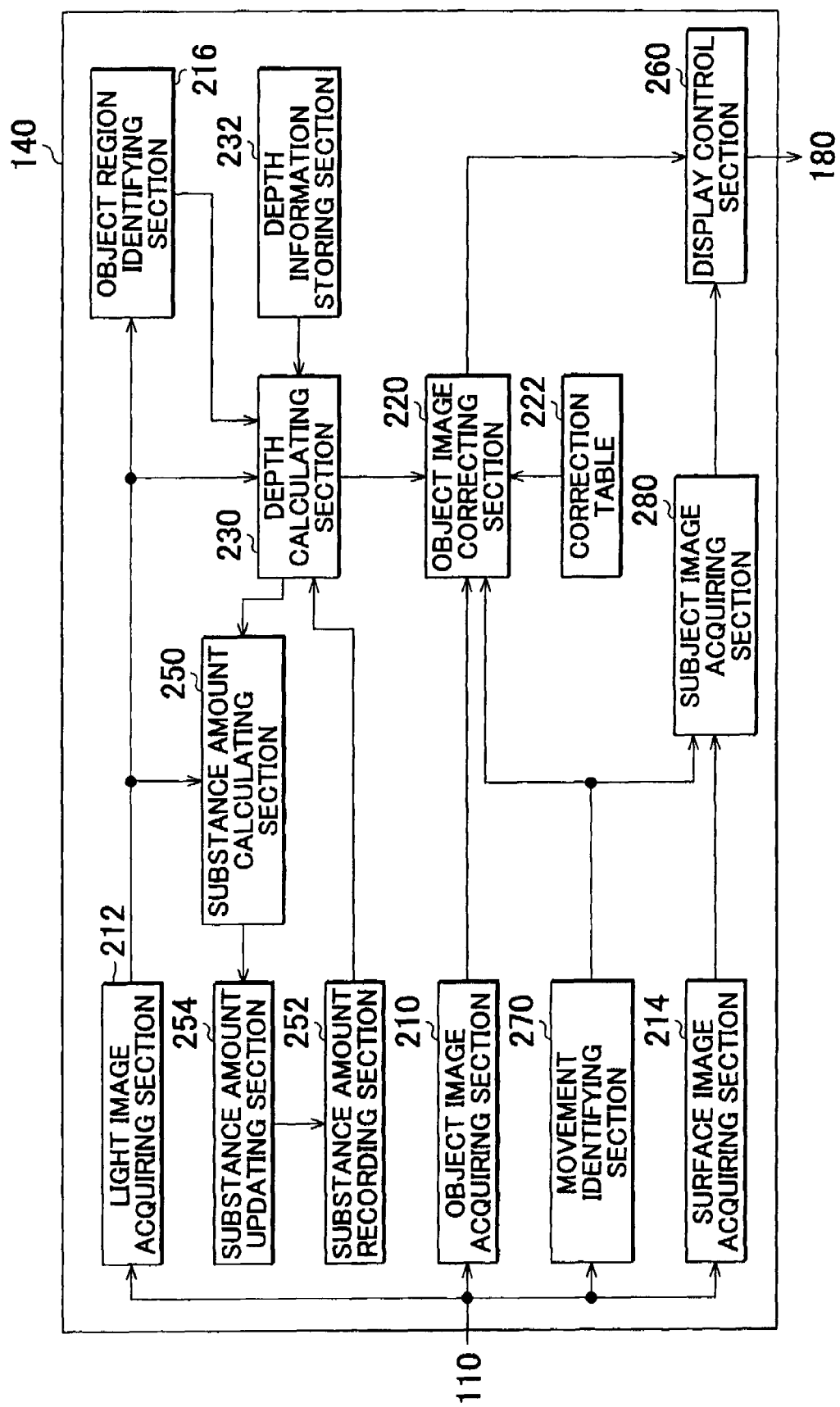
FIG. 2 shows an exemplary configuration of the image processing section 140.

Hereinafter, some embodiments of the present invention will be described. The embodiments do not limit the invention according to the claims, and all the combinations of the features described in the embodiments are not necessarily essential to means provided by aspects of the invention.

FIG. 1 shows an exemplary configuration of an image processing system 10 according to the present embodiment, along with a subject 20. The image processing system 10 calculates an amount of a substance in a blood vessel inside a subject 20, based on light, for example. The image processing system 10 is provided with an endoscope 100, an image processing section 140, an output section 180, a control section 105, a light irradiating section 150, and an ICG injecting section 190. In FIG. 1, section "A" is an enlarged view of the tip 102 of the endoscope 100. The control section 105 includes an image capturing control section 160 and a light emission control section 170.

The ICG injecting section 190 injects indo-cyanine green (ICG), which is a luminescent substance, into the subject 20, which is an example of the body in the present invention. The ICG is an example of the luminescent substance in the present embodiment, but the luminescent substance may instead be a different fluorescent substance. The ICG is excited by infrared rays with a wavelength of 750 nm, for example, to emit broad spectrum fluorescence centered at 810 nm.

If the subject 20 is a living organism, the ICG injecting section 190 injects the ICG into the blood vessels of the organism through intravenous injection. The image processing system 10 captures images of the blood vessels in the organism from the luminescent light of the ICG. This luminescent light is an example of the light from the body, and includes fluorescent light and phosphorescent light. The luminescent light includes chemical luminescence, frictional luminescence, and thermal luminescence, in addition to the luminescence from the excitation light or the like. The blood vessels are examples of the objects in the present invention.

The ICG injecting section 190 is controlled by the control section 105, for example, to inject the subject 20 with ICG such that the ICG concentration in the organism is held substantially constant. The subject 20 may be a human body. Objects such as blood vessels exist inside the subject 20. The image processing system 10 of the present embodiment detects an amount of a substance in the blood vessels, and also calculates the depth of blood vessels existing below the surface of the subject 20 based on the calculated substance amount, where the surface may be the inner surface of an organ. The image processing system 10 corrects the blur of the image of the object according to the detected depth.

The endoscope 100 includes an image capturing section 110, a light guide 120, and a clamp port 130. The image capturing section 110 includes a light receiving section 114 that receives the light from the subject 20, which is an example of the body. The tip 102 of the endoscope 100 includes an lens 112, which is a portion of the image capturing section 110, an irradiation aperture 124, which is a portion of the light guide 120, and a nozzle 138, which is a portion of the vibrating section 133.

A clamp 135 is inserted into the clamp port 130, and the clamp port 130 guides the clamp 135 to the tip 102. The tip of the clamp 135 may be any shape. Instead of the clamp, various types of instruments for treating the organism can be inserted into the clamp port 130. The nozzle 138 ejects water or air.

The light irradiating section 150 generates the light to be radiated from the tip 102 of the endoscope 100. The light generated by the light irradiating section 150 includes irradiation light that irradiates the subject 20 and excitation light, such as infra-red light, that excites the luminescent substance inside the subject 20 such that the luminescent substance emits luminescent light. The irradiation light may include a red component, a green component, and a blue component.

The image capturing section 110 captures a frame image based on the reflected light, which is the irradiation light reflected by the object, and the luminescent light emitted by the luminescent substance. The image capturing section 110 may include an optical system and a two-dimensional image capturing device such as a CCD, or may include the lens 112 in an optical system. If the luminescent substance emits infra-red light, the image capturing section 110 can capture an infra-red light frame image. If the light irradiating the object contains red, green, and blue components, i.e. if the irradiation light is white light, the image capturing section 110 can capture a visible light frame image.

The light from the object may be luminescent light such as fluorescent light or phosphorescent light emitted by the luminescent substance in the object, or may be the irradiation light that reflects from the object or that passes through the object. In other words, the image capturing section 110 captures a frame image of the object based on the light emitted by the luminescent substance inside of the object, the light reflected by the object, or the light passing through the object. The image capturing section 110 can receive each of the red component, the green component, the blue component, and the light in the wavelength region of the luminescent light separately by receiving the light at different times or at different places.

The light guide 120 may be formed of optical fiber. The light guide 120 guides the light emitted by the light irradiating section 150 to the tip 102 of the endoscope 100. The light guide 120 can have the irradiation aperture 124 provided in the tip 102. The light emitted by the light irradiating section 150 passes though the irradiation aperture 124 to irradiate the subject 20. The image capturing section 110 captures the image of the subject 20 using the light radiated from the irradiation aperture 124 and supplies the thus obtained image data to the image processing section 140.

The image processing section 140 processes the image data acquired from the image capturing section 110. The output section 180 outputs the image data processed by the image processing section 140. The image capturing control section 160 controls the image capturing by the image capturing section 110. The light emission control section 170 is controlled by the image capturing control section 160 to control the light irradiating section 150. For example, when the image capturing section 110 performs image capturing alternately with infra-red light and irradiation light, the light emission control section 170 controls the image capturing section 110 to synchronize the timing of the image capturing with the emission timing of the infra-red light and the irradiation light.

The image processing section 140 calculates the ICG concentration in the blood vessel that is at a position above a prescribed depth, based on the image of the blood vessel captured using visible light or captured using the luminescent light from the ICG. The image processing section 140 calculates the depth of a blood vessel positioned deeper in the body based on (i) an image of the deeper blood vessel captured using the luminescent light, (ii) an image of the deeper blood vessel captured using the visible light, and (iii) the ICG concentration. The image processing section 140 corrects the blur of the image of the blood vessel captured by the image capturing section 110, according to the calculated depth.

FIG. 2 shows an exemplary configuration of the image processing section 140. The image processing section 140 includes an object image acquiring section 210, a light image acquiring section 212, a surface image acquiring section 214, an object region identifying section 216, an object image correcting section 220, a correction table 222, a depth calculating section 230, a depth information storing section 232, a substance amount calculating section 250, a substance amount updating section 254, a substance amount storing section 252, a movement identifying section 270, a subject image generating section 280, and a display control section 260. The following describes the function of each element in the image processing section 140, along with the function and operation of other elements in the image processing system 10.

The light receiving section 114 receives light from the object, e.g. the blood vessel, existing inside the body. More specifically, the light receiving section 114 receives light in a plurality of wavelength regions from the object. For example, the light receiving section 114 receives red component light, blue component light, and green component light from the object. The light receiving section 114 may also receive infrared component light, which includes the light emitted by the luminescent substance inside the object. In this way, the light receiving section 114 receives light in a plurality of wavelength regions, including the wavelength region of the light emitted by the luminescent substance that is injected into the object.

The image capturing section 110 captures the image of the object based on the light from the object received by the light receiving section 114. More specifically, the image capturing section 110 captures the image of the object using the light in the plurality of wavelength regions from the object that is received by the light receiving section 114. The light image acquiring section 212 acquires, as the light image, the image of the object captured by the image capturing section 110 using the light in the plurality of wavelength regions.

If the light from the object includes the luminescent light emitted by the luminescent substance, the light image acquired by the light image acquiring section 212 includes an image of the object existing within a depth from the surface of the body to which the excitation light for exciting the luminescent substance can reach. For example, if the luminescent substance excitation light radiated from the tip 102 of the endoscope 100 has a wavelength of 750 nm, the excitation light can penetrate relatively deeply into the subject 20, i.e. to a depth of several centimeters. Therefore, the light image acquired by the light image acquiring section 212 can include the image of a blood vessel that is relatively deep in the subject 20. The blood vessel image is an example of the light image in the present invention.

The luminescent substance existing within the depth to which the excitation light can penetrate is excited by the excitation light, so that the light image acquired by the light image acquiring section 212 includes the image of the blood vessel existing within the depth to which the excitation light can penetrate. The image of the blood vessel becomes more blurred for a blood vessel that is deeper because the fluorescent light from the blood vessels is scattered by the subject 20.

If the light from the object includes the light reflected by the object, the light image acquired by the light image acquiring section 212 includes an image of the object existing within a depth in the body to which the irradiation light can penetrate and be reflected. Since the depth to which the irradiation light can penetrate depends on the wavelength of the irradiation light, green light can penetrate deeper into the body than blue light, and red light can penetrate deeper than both blue light and green light. Infra-red light can penetrate deeper into the body than red light. Therefore, the light image includes images of objects existing within a depth from the surface of the body to which the irradiation light in each wavelength region can penetrate and be reflected from.

In this way, the light image acquiring section 212 acquires a plurality of light images, each captured using the light in one of the plurality of different wavelength regions from the object, e.g. the blood vessel. These wavelength regions may be any wavelength regions, and are exemplified here by a red wavelength region centered on the red component of visible light, a green wavelength region centered on the green component of visible light, and a blue wavelength region centered on the blue component of visible light. The wavelength regions may instead be wavelength regions obtained by dividing the wavelength region of the fluorescent light from the ICG into a plurality of wavelength regions, such as a long wavelength region, a medium wavelength region, and a short wavelength region.

The depth calculating section 230 calculates the depth from the surface of the object existing inside the body. More specifically, the depth calculating section 230 calculates the depth of the object, e.g. the blood vessel, based on the content of the plurality of light images.

For example, the depth calculating section 230 detects the depth of the object, e.g. the blood vessel, in the subject 20 using the differences between the penetration depth of the light in different wavelength regions, or the absorption rate of the light in different wavelength regions in the subject 20. In other words, the depth calculating section 230 determines that a blood vessel that can be seen in the light image of the blue wavelength region exists in a range of depth to which the light in the blue wavelength region can penetrate and be reflected from. In the same way, the depth calculating section 230 determines that a blood vessel that can be seen in the light image of the green wavelength region exists in a range of depth to which the light in the green wavelength region can penetrate and be reflected from, and determines that a blood vessel that can be seen in the light image of the red wavelength region exists in a range of depth to which the light in the red wavelength region can penetrate and be reflected from.

In the plurality of wavelength regions of the fluorescent light emitted by the ICG in the blood vessel, the absorption rate of light in the long wavelength region is less than the absorption rate of the light in the short wavelength region, and therefore the depth calculating section 230 estimates the depth of the blood vessel based on the brightness of the blood vessel image in the light image obtained using the light in the long wavelength region, the medium wavelength region, or the short wavelength region. For example, if the blood vessel image in the image captured using the light in the short wavelength region is darker than the blood vessel image in the image captured using the light in the long wavelength region, the depth calculating section 230 determines that the blood vessel exists at a deep position in the body. On the other hand, if the blood vessel image in the image captured using the light in the short wavelength region is brighter than the blood vessel image in the image captured using the light in the long wavelength region, the depth calculating section 230 determines that the blood vessel exists at a shallow position in the body since the path of the light in which the light in the short wavelength region is absorbed is relatively short.

In this way, the depth calculating section 230 can detect the depth of the object, e.g. the blood vessel, using the difference in penetration depths, namely the penetration depth of the reflected light, of the light in different wavelengths. In this case, the light image acquiring section 212 may acquire, as the light image, the image of the light reflected from the object. The light image acquiring section 212 may acquire a plurality of light images using light in a plurality of different wavelength regions included in the white light that irradiates the object and is then reflected by the object. The light image acquiring section 212 may instead capture the plurality of light images by irradiating the object with light in a plurality of different wavelength regions and using the resulting reflected light to capture the light images.

If the depth calculating section 230 detects the depth of the object, e.g. the blood vessel, using the difference in the absorption rates of the different wavelength regions of the fluorescent light emitted from deep within the body, as described above, the light image acquiring section 212 acquires a plurality of light images using the light in the plurality of different wavelength regions included in the light emitted form the luminescent substance inside the body. The light irradiating the object is generated by the light irradiating section 150 and emitted through the irradiation aperture 124.

In this way, the depth calculating section 230 can calculate the depth of the object by comparing the brightness of the object in each light image, since the light images include information concerning the penetration depth of the light. For example, the object region identifying section 216 identifies an image region of the object in each light image. The depth calculating section 230 then calculates the depth of the object from the surface based on the brightness of the object image region identified by the object region identifying section 216.

The depth calculating section 230 may calculate the depth of the object based on a brightness ratio between the object image region in the image obtained using the light in the long wavelength region and the object image region in the image obtained using the light in the short wavelength region. The depth calculating section 230 may instead calculate the depth of the object based on the maximum brightness or the average brightness of the object image region.

As another example, the depth calculating section 230 may calculate the depth of the object based on a rate of change of the brightness at the edges of the object image region. The rate of change of the brightness can be expressed by a derivative of the brightness where the position (distance) in the image space is a variable, for example. This derivative is an example of the blur amount of the object in the object image region expressed as a number, and a large derivative indicates a small blur amount, which corresponds to an object at a shallow position.

The rate of change of the brightness can be expressed by a half-value width in a brightness distribution where the position (distance) in the image space is a variable, for example. A large half-value width indicates a large blur amount, and a small half-value width indicates an object at a shallow position. In this way, the depth calculating section 230 can calculate the depth of the object from the surface based on the amount of light in each of the plurality of wavelength regions received by the light receiving section 114.

The substance amount calculating section 250 calculates the amount of a substance in the object based on the content of the light image acquired by the light image acquiring section 212. More specifically, the substance amount calculating section 250 calculates the amount of the substance in the object based on a brightness value of each wavelength region in the light image. The "substance" in the object refers to a substance that emits light, a substance that reflects light or disperses light, or a substance that absorbs light. For example, the substance in the object may be a substance found in blood, such as the ICG in the blood vessel, oxidized hemoglobin, reduced hemoglobin, or bilirubin. In this way, the substance amount calculating section 250 can calculate the amount of the substance in the object emitting the light that is received by the light receiving section 114, based on the depth of the object calculated by the depth calculating section 230 and the amount of light received by the light receiving section 114.

If the depth of the object calculated by the depth calculating section 230 is less than a preset value, the substance amount calculating section 250 calculates the amount of the substance in the object based on the amount of light from the object received by the light receiving section 114 and the depth of the object calculated by the depth calculating section 230. In this way, the substance amount calculating section 250 calculates the amount of the substance in the object based on the depth calculated by the depth calculating section 230 and the amount of light from the object existing at a position shallower than a preset depth. The substance amount calculating section 250 can more accurately calculate the amount of the substance in a shallow object, because the effect of dispersion or the like on the measured value is small when calculating the amount of substance in an object at a shallow position.

The light receiving section 114 receives light from a second object that includes an amount of substance substantially equal to the amount of the substance in the above object, e.g. the first object. More specifically, the light receiving section 114 receives light in a plurality of wavelength regions from the second object. Even more specifically, the light receiving section 114 receives light in a plurality of wavelength regions including the light emitted from the luminescent substance inside the second object existing at a position deeper from the surface than the first object. For example, the light receiving section 114 receives light from a second blood vessel that is deeper than a first blood vessel. These blood vessels are connected throughout the body, and the blood component inside different blood vessels within the same organism can be considered as being substantially constant without regard to position, so that the ICG concentration can be considered as being constant regardless of the position of the blood vessel.

In this case, the depth calculating section 230 can calculate the depth of the second object from the surface based on the amount of light from the second object received by the light receiving section 114 and the amount of the substance calculated by the substance amount calculating section 250. More specifically, the depth calculating section 230 can calculate the depth of the second object based on the amount of light from the second object received by the light receiving section 114 in each of the plurality of wavelength regions and the amount of the substance calculated by the substance amount calculating section 250.

The depth calculating section 230 can calculate the depth of the second object based on (i) the amount of light in each of the plurality of wavelength regions received by the light receiving section 114 from the second object positioned deeper from the surface than the first object and (ii) the amount of the substance calculated by the substance amount calculating section 250. The deeper the first object, the greater the dispersion or absorption of the light between the first object and the surface. Therefore, when using light to simultaneously measure the amount of the substance in the object and the depth of the object, the error in the measured value increases. However, by using the image processing system 10, the depth of an object at a deep position can be accurately calculated by using the concentration of the substance in an object at a shallow position.

Here, a luminescent substance such as ICG is used as an example of the substance. That is, the substance amount calculating section 250 calculates the amount of the luminescent substance inside the object based on the amount of light from the luminescent substance received by the light receiving section 114 and the depth of the object calculated by the depth calculating section 230. The depth calculating section 230 then calculates the depth of the second object based on (i) the amount of light in each of the plurality of wavelength regions from the second object received by the light receiving section 114 and (ii) the amount of the luminescent substance calculated by the substance amount calculating section 250.

The depth information storing section 232 stores the depth of the object from the surface of the body in association with the amount of the luminescent substance inside the object and the amount of light from the object in each of the plurality of wavelength regions. More specifically, the depth information storing section 232 stores the depth of the object from the surface of the body in association with the concentration of the luminescent substance inside the object and the amount of light from the object in each of the plurality of wavelength regions. The depth calculating section 230 calculates the depth of the second object based on (i) the amount of light in each of the plurality of wavelength regions from the second object received by the light receiving section 114, (ii) the amount of the luminescent substance calculated by the substance amount calculating section 250, and (iii) the depth stored by the depth information storing section 232.

The substance amount storing section 252 stores therein the amount of the luminescent substance inside the object calculated by the substance amount calculating section 250. The depth calculating section 230 can calculate the depth of the second object based on the amount of the substance stored by the substance amount storing section 252 and the amount of light in each of the plurality of wavelength regions from the second object received by the light receiving section 114. The substance amount calculating section 250 calculates the amount of the luminescent substance injected into the object. In this case, on the condition that a new luminescent substance amount calculated by the substance amount calculating section 250 differs from the luminescent substance amount stored in the substance amount storing section 252 by more than a preset amount, the substance amount updating section 254 updates the luminescent substance amount stored in the substance amount storing section 252 to be the new amount calculated by the substance amount calculating section 250.

If the body is a living organism, the injected luminescent substance is metabolized in the body over time, and therefore concentration of the luminescent substance in the blood might gradually decrease over time. If necessary, the ICG injecting section 190 may repeatedly inject the luminescent substance into the body to compensate for the decrease in the concentration. The image processing system 10 can calculate the depth with consideration to the change in the concentration of the substance caused by reasons such as that described above. Accordingly, even if there is an error in the value calculated by the substance amount calculating section 250 due to noise or the like, the amount of that error reflected in the depth can be prevented from becoming excessively large.

The object image acquiring section 210 acquires an object image captured using the light from the object. The image capturing section 110 captures an image of the object through the surface of the body. The object image acquiring section 210 acquires the image of the object captured through the surface. For example, the object image acquiring section 210 acquires the object image that is captured by the image capturing section 110 using the luminescent light from the object.

The object image correcting section 220 corrects the object image acquired by the object image acquiring section 210, based on the depth of the second object calculated by the depth calculating section 230. More specifically, the object image correcting section 220 corrects the spread of the object image resulting from the light from the object traveling to the surface, based on the depth of the second object calculated by the depth calculating section 230.

The image corrected by the object image correcting section 220 is supplied to the output section 180, and the output section 180 displays the corrected image. The correction table 222 stores a correction value for correcting the spread of the object image in association with the depth of the object from the surface. The object image correcting section 220 corrects the spread of the object image based on the correction value stored in the correction table 222 and the depth calculated by the depth calculating section 230.

The surface image acquiring section 214 acquires an image of the surface of the body captured by the image capturing section 110, for example. That is, the surface image acquiring section 214 acquires an image that is equivalent to an image seen by the naked eye. For example, the surface image acquiring section 214 acquires, as the surface image, the image captured by the image capturing section 110 using the irradiation light reflected from the surface of the body. More specifically, the surface image acquiring section 214 may acquire, as the surface image, the image captured by the image capturing section 110 using the irradiation light, e.g. white light, reflected from the surface of the body.

The image capturing section 110 may capture the surface image and the object image at different timings. For example, the image capturing section 110 may capture the object image by capturing a series of visible light surface images while irradiating the body with white light and irradiating the body with the excitation light instead of the white light at prescribed timings. In this case, the movement identifying section 270 identifies the movement of the object between the timing at which the excitation light is radiated and the timing at which the white light is irradiated. The subject image generating section 280 generates the surface image that is expected to be obtained when the excitation light is radiated, based on the surface image obtained when the white light is radiated and the movement identified by the movement identifying section 270. The function and operation of the control section 105, the image capturing section 110, the light irradiating section 150, the movement identifying section 270, and the subject image generating section 280 when capturing the object image and the surface image at separate timings are described in detail in relation to FIG. 8 and onward.

The display control section 260 controls the display of the surface image and the corrected image on the output section 180. For example, the display control section 260 controls the display of the object image corrected by the object image correcting section 220, according to the depth calculated by the depth calculating section 230. More specifically, the display control section 260 changes the brightness or color of the object image corrected by the object image correcting section 220, according to the depth calculated by the depth calculating section 230, and displays the thus changed image on the output section 180. The display control section 260 may instead display the surface image together with the corrected image on the output section 180. As another example, the display control section 260 may display the information concerning the depth of the object on the output section 180 as a numeric value.

The depth calculating section 230 may calculate the depth from the surface for each of a plurality of objects. The object image correcting section 220 may correct the spread of the image of each of the plurality of objects in the object image, based on the depth of each object.

Figure 3:
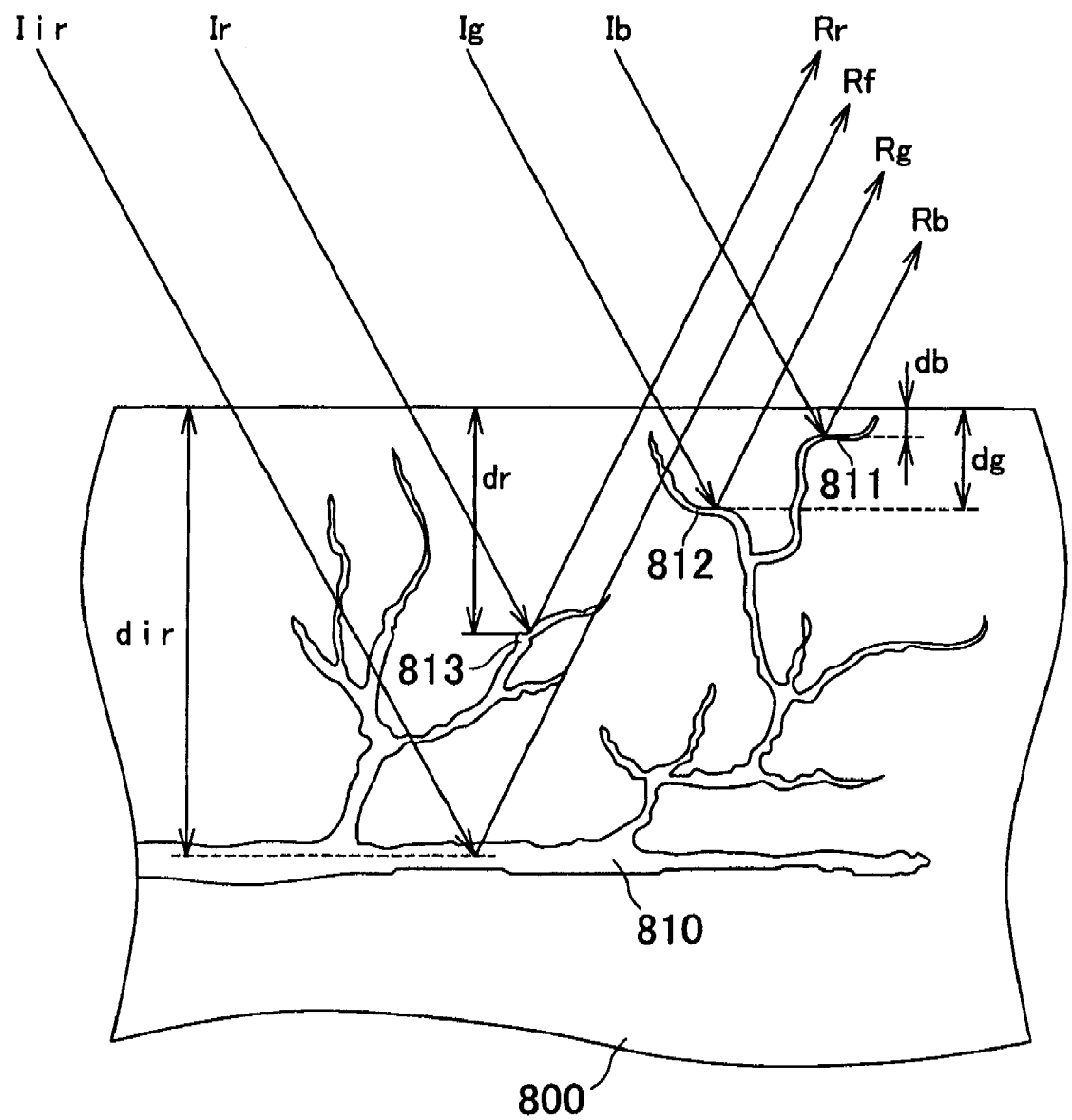
FIG. 3 shows a typical state of light reflected inside the subject 20.

FIG. 3 shows a typical state of light reflected inside the subject 20. Blood vessels 810 to 813 are examples of the objects inside the subject 20. These depth of these blood vessels increases in the order of blood vessel 811, blood vessel 812, blood vessel 813, and blood vessel 810. The ICG injecting section 190 injects the ICG, which is the luminescent substance, into the blood vessel 810, so that the ICG flows through the blood vessels 810 to 813.

The subject 20 is irradiated with infra-red light Iir, which is the ICG excitation light, and red light Ir, green light Ig, and blue light Ib, which are the components of the irradiation light irradiating the blood vessels. The infra-red light Iir can penetrate the subject 20 to a relatively deep position shown by the depth dir, thereby exciting the ICG that is in blood vessels within the depth dir from the surface, for example the blood vessel 810. Accordingly, the blood vessels 811 to 813 that are shallower than the depth dir are captured in the object image using the fluorescent light Rf from the ICG. The images of the blood vessels in the acquired object image are blurred.

The red light Ir penetrates to a depth dr and is reflected near the depth dr. Accordingly, the resulting reflected red light Rr includes image information of the blood vessel 813 near the depth dr. The image of the blood vessel 813 obtained using the reflected red light Rr is acquired as the light image resulting from light in the red wavelength region. This light image includes the image of the blood vessel near the depth dr.

The green light Ig penetrates to a depth dg and is reflected near the depth dg. Accordingly, the resulting reflected green light Rg includes image information of the blood vessel 812 near the depth dg. The image of the blood vessel 812 obtained using the reflected green light Rg is acquired as the light image resulting from light in the green wavelength region. This light image includes the image of the blood vessel near the depth dg.

The blue light Ib penetrates to a depth db and is reflected near the depth db. Accordingly, the resulting reflected blue light Rb includes image information of the blood vessel 811 near the depth db. The image of the blood vessel 811 obtained using the reflected blue light Rb is acquired as the light image resulting from light in the blue wavelength region. This light image includes the image of the blood vessel near the depth db.

As described above, the depth calculating section 230 can calculate the depth of the blood vessel 811 at a shallow position based on the light images resulting from each of the reflected red light Rr, the reflected green light Rg, and the reflected blue light Rb, for example. The depth calculating section 230 can then calculate the depth of the blood vessels 812, 813, and 810 captured using the fluorescent light Rf, based on the ICG concentration calculated by the substance amount calculating section 250 and the depth of the blood vessel 811. The object image correcting section 220 can correct the spread of the images of the blood vessels 810 to 813 according to the calculated depths.

Figure 4:
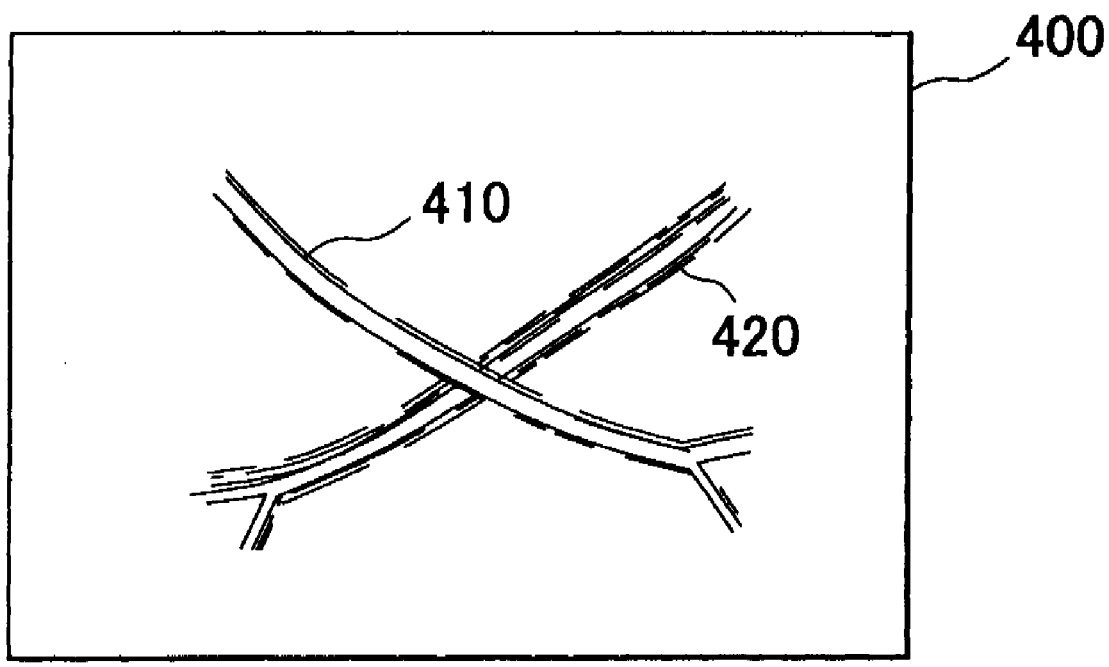
FIG. 4 shows an example of captured blood vessel images.

FIG. 4 shows an example of captured blood vessel images. The blood vessel image 410 is the image of a shallow blood vessel, and the blood vessel image 420 is the image of a blood vessel deeper than the blood vessel shown by the blood vessel image 410. As shown in FIG. 4, the blur amount of the blood vessel image 410 is less than the blur amount of the blood vessel image 420.

FIG. 5 is a table showing exemplary data stored in the depth information storing section 232. The depth information storing section 232 stores, in association with the intensity of each light component from the blood vessel, the relative intensities $I_{IR}$, $I_R$, $I_G$, and $I_B$, the ICG concentration $C_{ICG}$, and the depth $D_a$ of the blood vessel. Here, $I_{IR}$, $I_R$, $I_G$, and $I_B$ represent the relative intensities of the infra-red light component, the red light component, the green light component, and the blue light component, respectively.

As described above, the depth calculating section 230 can calculate the depth of a blood vessel based on the image of a shallower blood vessel, e.g. the blood vessel 811. The substance amount calculating section 250 calculates the ICG concentration in a blood vessel based on the relative intensities of the red component, the green component, the blue component, and the infra-red component shown by the image, the depth calculated by the depth calculating section 230, and the data stored in the depth information storing section 232. For example, the substance amount calculating section 250 calculates the ICG concentration in the blood vessel to be the ICG concentration stored in the depth information storing section 232 in association with the relative intensities of the red component, the green component, the blue component, and the infra-red component shown by the image, and the depth calculated by the depth calculating section 230. If the depth information storing section 232 does not store information corresponding to each measurement value, the substance amount calculating section 250 can calculate the ICG concentration by interpolating or extrapolating the data stored in the depth information storing section 232.

When calculating the depth of the blood vessel 810 that is deeper than the shallow blood vessel, the depth calculating section 230 calculates the depth of this deep blood vessel based on the ICG concentration calculated for the shallow blood vessel and the relative intensities of the red component, the green component, the blue component, and the infra-red component shown by the image. For example, the depth calculating section 230 calculates the depth of the deep blood vessel to be the depth stored in the depth information storing section 232 in association with the ICG concentration calculated by the substance amount calculating section 250 and the relative intensities of the red component, the green component, the blue component, and the infra-red component shown by the image. If the depth information storing section 232 does not store information corresponding to each measurement value, the depth calculating section 230 can calculate the depth by interpolating or extrapolating the data stored in the depth information storing section 232.

Figure 6:
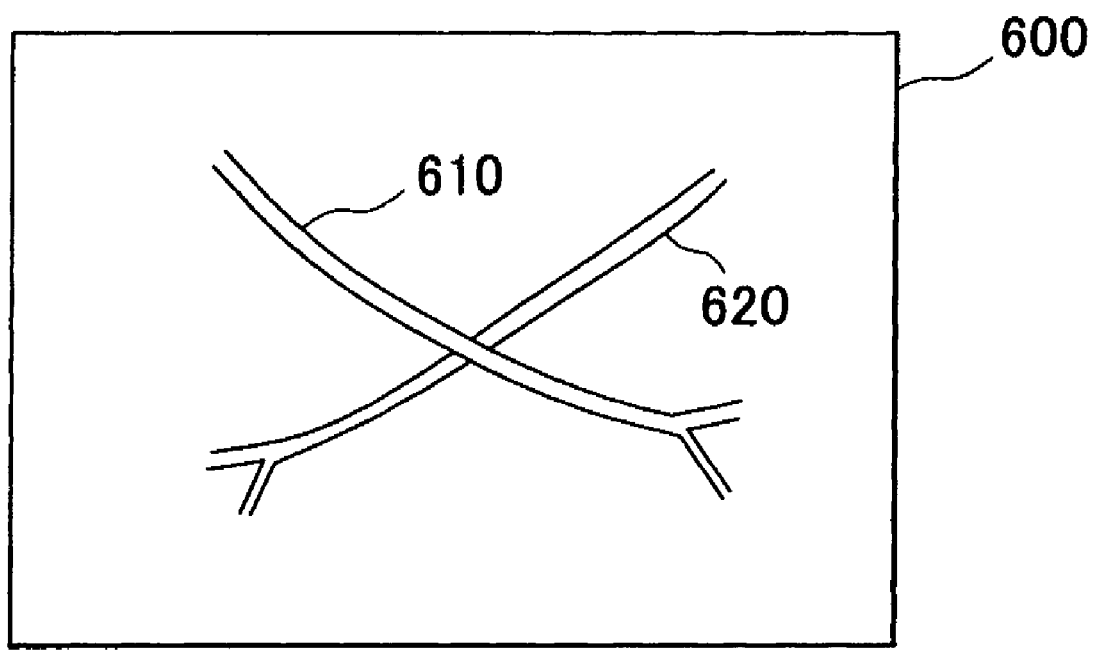
FIG. 6 shows an exemplary image 600 containing corrected blood vessel images 610 and 620.

FIG. 6 shows an exemplary image 600 containing corrected blood vessel images 610 and 620. A scattered image, which is caused by a point light source being scattered between the object in the body and the surface of the body, can be expressed by a point-spread function having the depth of the point light source as a parameter. The object image correcting section 220 uses an inverse filter of the point-spread function according to the depth of the object to correct the blur of the blood vessel image.

The correction table 222 may store the inverse filter of the point-spread function in association with the depth. The object image correcting section 220 corrects each blood vessel image identified by the object region identifying section 216 by using the inverse filter stored in the correction table 222 in association with the depth of the blood vessel calculated by the depth calculating section 230. In this way, the blur of the blood vessel image 410 can be corrected to achieve the blood vessel image 610 and the blur of the blood vessel image 420 can be corrected to achieve the blood vessel image 620.

The display control section 260 indicates the depth of the objects on the output section 180 by changing the contrast or the color, for example, of the blood vessel images 610 and 620. Use of the image processing system 10 of the present invention enables a doctor who is watching the output section 180 while performing surgery, for example, to clearly view images of the internal blood vessels that cannot be seen by the naked eye, and also enables the doctor to see information concerning the depth of the blood vessels.

Figure 7:
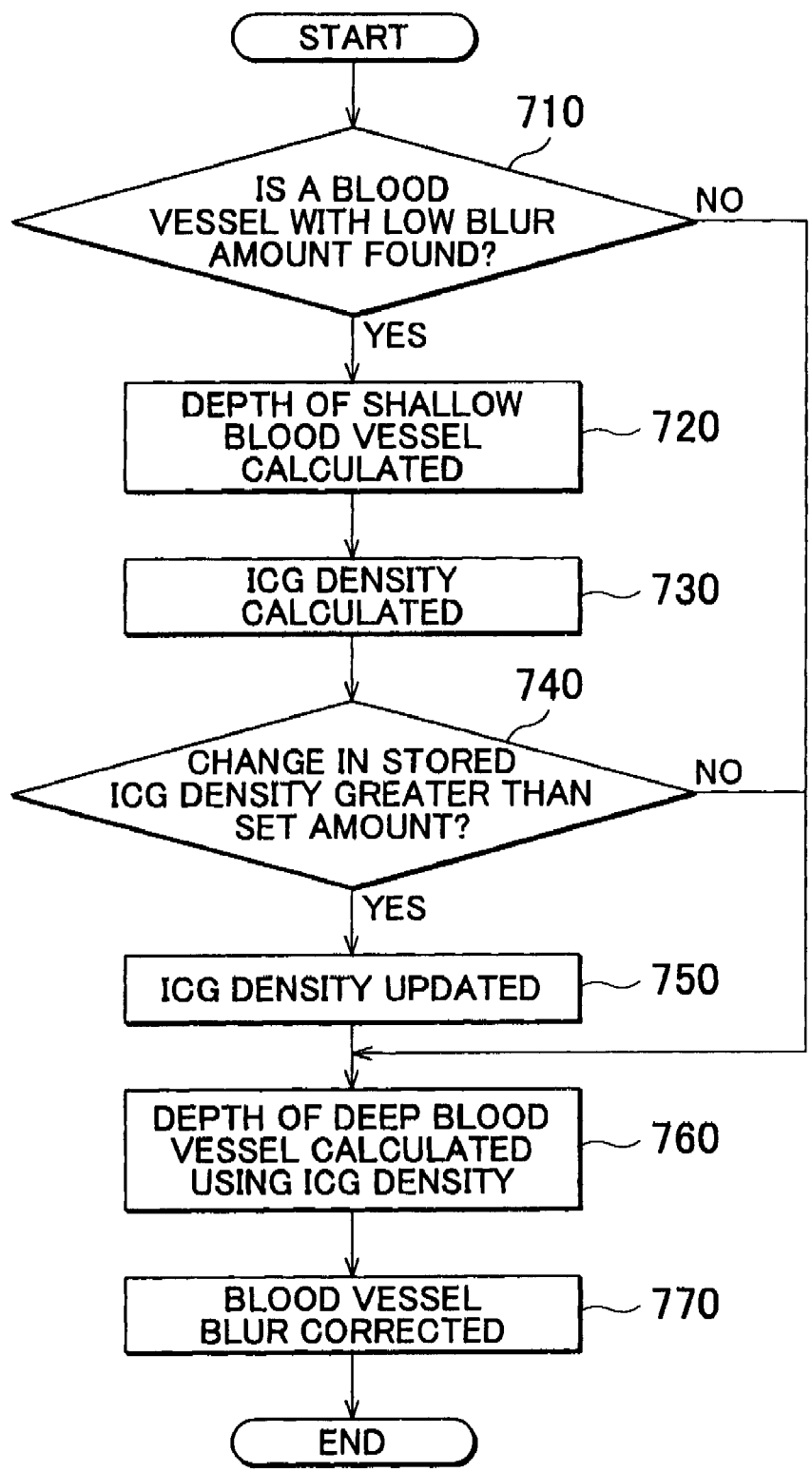
FIG. 7 shows an exemplary process flow of the image processing system 10.

FIG. 7 shows an exemplary process flow of the image processing system 10. The object image acquiring section 210 acquires the blood vessel images in series at prescribed intervals. The depth calculating section 230 judges whether a blood vessel exists whose blur amount is less than a preset value (S710). If the depth calculating section 230 judges at S710 that a blood vessel exists whose blur amount is less than the preset value, the process moves on to S720.

The blur amount is an example of an indicator for judging whether a shallow blood vessel is present, but other methods for detecting a shallow blood vessel may be used. For example, as described in relation to FIG. 3, the depth calculating section 230 may calculate the depth based on the intensity of light in a plurality of wavelength regions, and then judge at S710 whether the calculated depth is less than the preset value.

The depth calculating section 230 calculates the depth of the shallow blood vessel based on the blur amount of the blood vessel image or the intensity of light in the plurality of wavelength regions, as described above. As described in relation to FIG. 5, the substance amount calculating section 250 then calculates the ICG concentration based on the depth of the shallow blood vessel calculated by the depth calculating section 230 (S730). The substance amount updating section 254 judges whether the ICG concentration calculated by the substance amount calculating section 250 is less than the ICG concentration stored in the substance amount storing section 252 (S740).

If the substance amount updating section 254 judges at S740 that the ICG concentration calculated by the substance amount calculating section 250 differs from the ICG concentration stored in the substance amount storing section 252 by an amount greater than or equal to a preset value, the substance amount updating section 254 stores the ICG concentration calculated by the substance amount calculating section 250 in the substance amount storing section 252 (S750). In this way, the substance amount updating section 254 updates the ICG concentration stored in the substance amount storing section 252 to be the new ICG concentration calculated by the substance amount calculating section 250, and the process then moves on to S760. If the substance amount updating section 254 judges at S740 that the absolute value of the difference between the ICG concentration calculated by the substance amount calculating section 250 and the ICG concentration stored in the substance amount storing section 252 is less than the preset value, the process skips S750 and moves directly on to S760.

The depth calculating section 230 calculates the depth of each blood vessel based on the ICG concentration stored in the substance amount storing section 252 (S760). The object image correcting section 220 corrects the blur of each blood vessel image (S770) and supplies the corrected blood vessel images to the display control section 260. If the depth calculating section 230 judges at S710 that a blood vessel whose blur amount is less than the preset value does not exist, the process moves directly to S760.

By calculating the ICG concentration based on a shallow blood vessel image in this way, the image processing system 10 can more accurately calculate the ICG concentration. Furthermore, by updating the ICG concentration on the condition that the calculated ICG concentration differs from the stored ICG concentration by more than a prescribed amount and then using the new ICG concentration to calculate the depth of a deep blood vessel, the image processing system 10 can more accurately calculate the depth of a deep blood vessel.

If the ICG concentration is not updated at S750, that is, if the judgment at S740 or S710 is "NO," the depth calculating section 230 may calculate the current ICG concentration by subtracting, from the ICG concentration stored in the substance amount storing section 252, an ICG concentration proportional to the time that elapsed from (i) the time at which the ICG concentration stored in the substance amount storing section 252 was calculated to (ii) the current time. The depth calculating section 230 may calculate the depth of a deeper blood vessel using the thus calculated ICG concentration.

The substance amount storing section 252 may record the plurality of timings at which the ICG concentration is calculated. The depth calculating section 230 may calculate the current ICG concentration by performing a temporal extrapolation or the like based on the ICG concentration at the plurality of timings and the current time. If the ICG concentration stored in the substance amount storing section 252 becomes less than a prescribed value, the control section 105 may control the ICG injecting section 190 to inject the subject 20 with the ICG.

FIG. 8 shows an exemplary configuration of the image capturing section 110. The image capturing section 110 includes the lens 112, an image capturing device 810, a spectral filter section 820, and a lens-side excitation light cut filter 830. The image capturing device 810 includes a plurality of first light receiving elements 851 including a first light receiving element 851a, a plurality of second light receiving elements 852 including a second light receiving element 852a and a second light receiving element 852b, and a plurality of third light receiving elements 853 including a third light receiving element 853a.

The following describes the function and operation of the configurational elements in the image capturing section 110. For the sake of simplicity, the following description refers to a single first light receiving element 851, a single second light receiving element 852, and a single third light receiving element 853. Furthermore, the plurality of first light receiving elements 851, second light receiving elements 852, and third light receiving element 853 may be referred to simply as "the light receiving elements."

The first light receiving element 851, the second light receiving element 852, and the third light receiving element 853 receive light from the subject via the lens 112. More specifically, the first light receiving element 851 receives light in a specified wavelength region and light in a first wavelength region, which is different from the specified wavelength region. The specified wavelength region may be the wavelength region of the luminescent light or the wavelength region of infra-red light, for example. The second light receiving element 852 receives light in a second wavelength region, which is different from the specified wavelength region. The third light receiving element 853 receives light in a third wavelength region, which is different from the specified wavelength region, the first wavelength region, and the second wavelength region.

The first wavelength region, the second wavelength region, and the third wavelength region are each different wavelength regions that do not overlap with each other. The first light receiving element 851, the second light receiving element 852, and the third light receiving element 853 are arranged 2-dimensionally in a prescribed pattern.

The spectral filter section 820 includes a plurality of filter elements that each allow one of the light in the first wavelength region, the light in the second wavelength region, and the light in the third wavelength region to pass through. The filter elements are arranged 2-dimensionally to correspond respectively to the first light receiving element 851, the second light receiving element 852, and the third light receiving element 853. Each light receiving element receives the light that passes through the corresponding filter element. In this way, the first light receiving element 851, the second light receiving element 852, and the third light receiving element 853 each receive light in a different wavelength region.

The lens-side excitation light cut filter 830 is provided at least between (i) the subject and (ii) the second light receiving element 852 and the third light receiving element 853, and cuts the light in the wavelength region of the excitation light. The second light receiving element 852 and the third light receiving element 853 receive the light reflected by the subject through the lens-side excitation light cut filter 830. Therefore, the second light receiving element 852 and the third light receiving element 853 do not substantially receive the light resulting from the excitation light being reflected by the subject.

The lens-side excitation light cut filter 830 may cut the light in the wavelength region of the excitation light and the light in the specified wavelength region. In this case, the second light receiving element 852 and the third light receiving element 853 do not substantially receive the luminescent light from the subject, for example.

The lens-side excitation light cut filter 830 may be provided between the subject and the first light receiving element 851. In this case, the lens-side excitation light cut filter 830 allows light in the specified wavelength region to pass through.

In the same manner as the spectral filter section 820, the lens-side excitation light cut filter 830 may include filter elements that are arranged 2-dimensionally corresponding respectively to the first light receiving element 851, the second light receiving element 852, and the third light receiving element 853. The filter element supplying light to the first light receiving element 851 allows at least light in the first wavelength region and light in the specified wavelength region to pass through. The filter element supplying light to the first light receiving element 851 may cut the light in the wavelength region of the excitation light. The filter element supplying light to the second light receiving element 852 cuts the light in the wavelength region of the excitation light and the light in the specified wavelength region, and allows at least the light in the second wavelength region to pass through. The filter element supplying light to the third light receiving element 853 cuts the light in the wavelength region of the excitation light and the light in the specified wavelength region, and allows at least the light in the third wavelength region to pass through.

The image processing section 140 determines the pixel value for a single pixel based on at least the amount of light received by the first light receiving element 851a, the second light receiving element 852a, the second light receiving element 852b, and the third light receiving element 853a. In other words, the first light receiving element 851a, the second light receiving element 852a, the second light receiving element 852b, and the third light receiving element 853a are arranged 2-dimensionally to form a single pixel element, and a plurality of pixel elements are formed by 2-dimensionally arranging a plurality of such groups of light receiving elements forming a single pixel element. The light receiving elements are not limited to the arrangement shown in FIG. 8, and may instead be arranged in a variety of different arrangements.

FIG. 9 shows exemplary spectral sensitivity characteristics of the first light receiving element 851, the second light receiving element 852, and the third light receiving element 853. The line 930, the line 910, and the line 920 represent the spectral sensitivity distributions of the first light receiving element 851, the second light receiving element 852, and the third light receiving element 853, respectively. For example, the first light receiving element 851 is sensitive to light having a wavelength around 650 nm, and the other light receiving elements are not substantially sensitive to this light. The second light receiving element 852 is sensitive to light having a wavelength around 450 nm, and the other light receiving elements are not substantially sensitive to this light. The third light receiving element 853 is sensitive to light having a wavelength around 550 nm, and the other light receiving elements are not substantially sensitive to this light.

The first light receiving element 851 can receive the light in the infra-red spectrum, i.e. 810 nm, which is an example of the specified wavelength region. This spectral sensitivity characteristic depends on the transmission characteristics of the lens-side excitation light cut filter 830 and the spectral filter section 820 and the spectral sensitivity of each light receiving element.

In this way, the first light receiving element 851, the second light receiving element 852, and the third light receiving element 853 receive the red component, the green component, and the blue component of light, respectively. The first light receiving element 851 can also receive the light in the infra-red spectrum, which is an example of the specified wavelength region. The first light receiving element 851, the second light receiving element 852, and the third light receiving element 853 may be image capturing elements such as CCDs, CMOSs, or the like. The spectral sensitivity characteristics of the first light receiving element 851, the second light receiving element 852, and the third light receiving element 853, as represented by the line 930, the line 910, and the line 920, are obtained by a combination of the spectral transmission factor of the lens-side excitation light cut filter 830, the spectral transmission factors of the filter elements in the spectral filter section 820, and the spectral sensitivity of the image capturing elements themselves.

Figure 10:
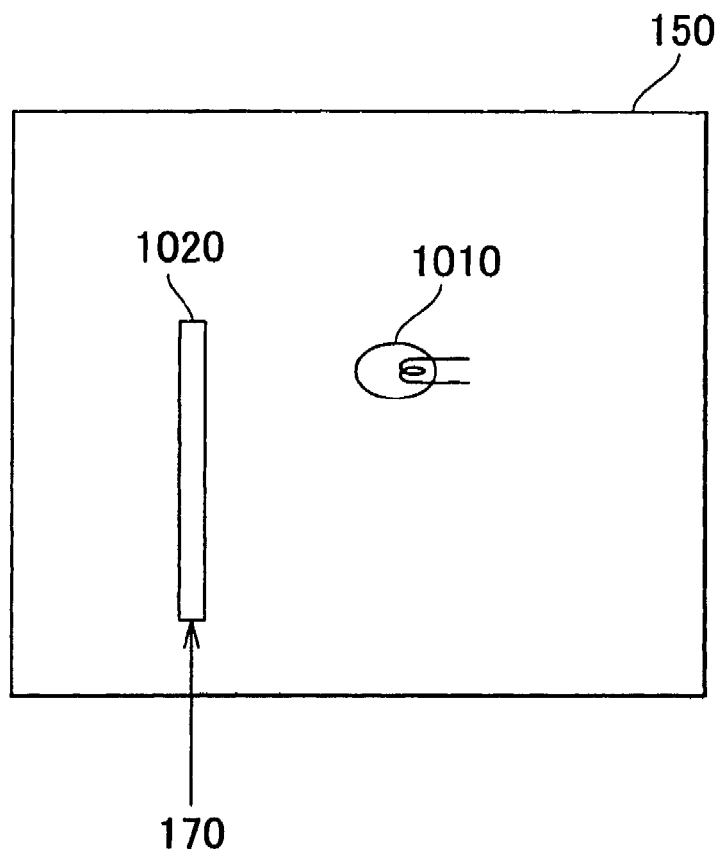
FIG. 10 shows an exemplary configuration of the light irradiating section 150.

FIG. 10 shows an exemplary configuration of the light irradiating section 150. The light irradiating section 150 includes a light emitting section 1010 and a light source filter section 1020. The light emitting section 1010 emits light in a wavelength region that includes the wavelength region of the excitation light, the first wavelength region, the second wavelength region, and the third wavelength region. The light emitting section 1010 of the present embodiment may be a xenon lamp.

Figure 11:
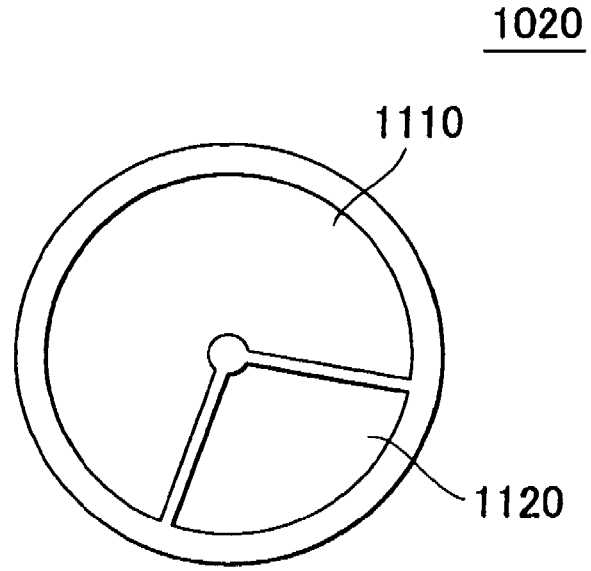
FIG. 11 shows an exemplary configuration of the light source filter section 1020 as seen from the direction in which the light is guided from the light emitting section 1010.

FIG. 11 shows an exemplary configuration of the light source filter section 1020 as seen from the direction in which the light is guided from the light emitting section 1010. The light source filter section 1020 includes an irradiation light cut filter section 1120 and an excitation light cut filter section 1110. The light emission control section 170 rotates the light source filter section 1020 in a plane substantially perpendicular to the direction in which the light emitted by the light emitting section 1010 travels, with the central axis of the light source filter section 1020 serving as the center of rotation.

The excitation light cut filter section 1110 cuts the light in the wavelength region of the excitation light, and allows the light in the first wavelength region, the light in the second wavelength region, and the light in the third wavelength region to pass through. The irradiation light cut filter section 1120 allows the light in the wavelength region of the excitation light, the light in the second wavelength region, and the light in the third wavelength region to pass through. The irradiation light cut filter section 1120 desirably cuts the light in the first wavelength region. The light from the light emitting section 1010 is guided to a position shifted from the central axis of the light source filter section 1020.

Accordingly, when the light from the light emitting section 1010 is guided to the excitation light cut filter section 1110, the excitation light cut filter section 1110 cuts the light in the wavelength region of the excitation light and allows the light in the first wavelength region, the light in the second wavelength region, and the light in the third wavelength region to pass through. Therefore, at this time, the subject is substantially irradiated with the light in the first wavelength region, the light in the second wavelength region, and the light in the third wavelength region.

On the other hand, when the light from the light emitting section 1010 is guided to the irradiation light cut filter section 1120, the light in the wavelength region of the excitation light, the light in the second wavelength region, and the light in the third wavelength region are allowed to pass through the irradiation light cut filter section 1120. Therefore, at this time, the subject is irradiated with the excitation light, the light in the second wavelength region, and the light in the third wavelength region.

The image capturing section 110 is controlled by the image capturing control section 160 to receive the visible light reflected by the subject 20 while the visible light is being emitted, where the visible light is the light in the first wavelength region, the light in the second wavelength region, and the light in the third wavelength region. The surface image acquiring section 214 generates a visible light image of the subject, which is an example of the surface image, based on the amount of light received by the image capturing section 110. If the radiated light is substantially white light, the surface image can be a white light image.

Furthermore, the image capturing section 110 is controlled by the image capturing control section 160 to receive the luminescent light emitted by the ICG inside the subject, the light in the second wavelength region reflected by the subject 20, and the light in the third wavelength region reflected by the subject 20, while the excitation light, the second wavelength region, and the third wavelength region are being emitted. The object image acquiring section 210 acquires a signal from the first light receiving element 851 corresponding to the amount of light received by the first light receiving element 851 to generate the luminescent light image of the subject based on the amount of luminescent light received by the first light receiving element 851. The surface image acquiring section 214 generates the visible light subject image based on (i) the amount of light in the second wavelength region and the amount of light in the third wavelength region as indicated by the signals from the second light receiving element 852 and the third light receiving element 853 and (ii) the amount of light in the first wavelength region received by the first light receiving element 851 at another timing.

Figure 12:
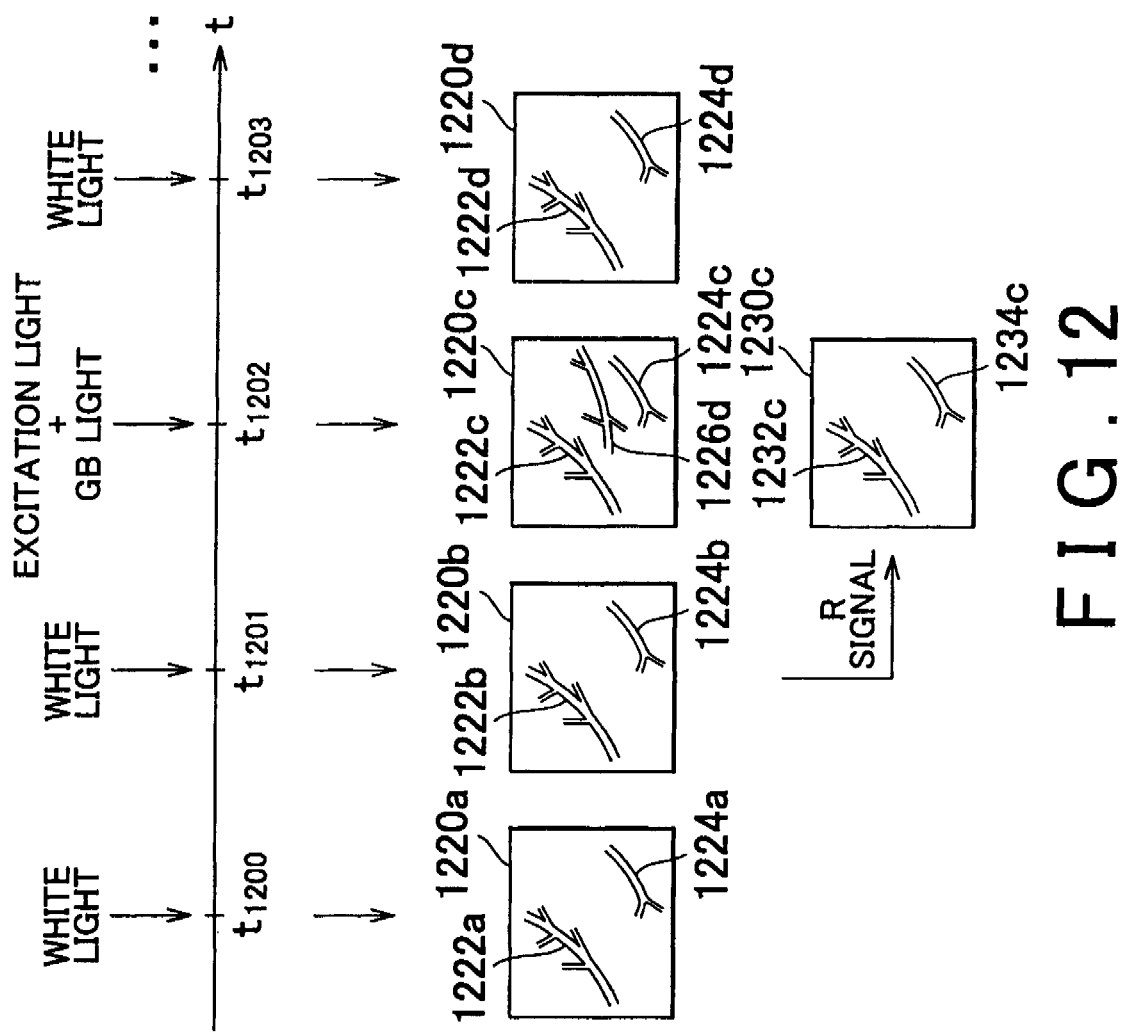
FIG. 12 shows the timing of the image capturing by the image capturing section 110 and exemplary images generated by the image processing section 140.

FIG. 12 shows the timing of the image capturing by the image capturing section 110 and exemplary images generated by the image processing section 140. The image capturing control section 160 causes the image capturing section 110 to capture images based on the light from the object at times t1200, t1201, t1202, t1203, etc. The light emission control section 170 is controlled by the image capturing control section 160 to irradiate the subject with the light emitted by the light emitting section 1010 through the excitation light cut filter section 1110, at first timings that include t1200, t1201, and t1203. In this way, the light emission control section 170 controls the light irradiating section 150 to irradiate the subject with light in a wavelength region including the first wavelength region, the second wavelength region, and the third wavelength region at the first timings.

At the first timings, the image capturing control section 160 irradiates the subject with light in a wavelength region including the first wavelength region, the second wavelength region, and the third wavelength region. The image capturing control section 160 separates the light reflected from the object such that the first light receiving element 851 receives the light in the first wavelength region, the second light receiving element 852 receives the light in the second wavelength region, and the third light receiving element 853 receives the light in the third wavelength region. In this way, the image capturing control section 160 causes the first light receiving element 851 to receive the light in the first wavelength region, causes the second light receiving element 852 to receive the light in the second wavelength region, and causes the third light receiving element 853 to receive the light in the third wavelength region, at the first timings.

At second timings, which include t1202, the image capturing control section 160 controls the light emission control section 170 to irradiate the subject with the light emitted by the light emitting section 1010 through the irradiation light cut filter section 1120. In this way, the light emission control section 170 controls the light irradiating section 150 to irradiate the subject with the excitation light and the light in the wavelength region including the second wavelength region and the third wavelength region at the second timings.

The image capturing control section 160 causes the first light receiving element 851 to receive light in the specified wavelength region emitted from the subject at the second timings. In other words, the image capturing control section 160 causes the first light receiving element 851 to receive the light in the specified wavelength region from the subject at the second timings.

In this way, the control section 105 irradiates the subject with the excitation light, the light in the second wavelength region, and the light in the third wavelength region at the second timings, but does not irradiate the subject with the light in the first wavelength region. At this time, the first light receiving element 851 receives the light in the specified wavelength region emitted by the subject, the second light receiving element 852 receives the light in the second wavelength region reflected from the subject, and the third light receiving element 853 receives the light in the third wavelength region reflected from the subject. The wavelength region of the excitation light is different from the first wavelength region, the second wavelength region, and the third wavelength region, and has a wavelength region that does not overlap with the first wavelength region, the second wavelength region, or the third wavelength region.

As described above, the control section 105 controls the wavelength region of the light received by the first light receiving element 851, the second light receiving element 852, and the third light receiving element 853. The image processing section 140 generates the image using the light in each wavelength region, based on the amount of light received by the light receiving elements at the plurality of timings.

The surface image acquiring section 214 generates a subject image 1220a, a subject image 1220b, and a subject image 1220d based on the amount of light received by the light receiving elements at the first timings represented by t1200, t1201, and t1203, respectively. The subject image 1220a, the subject image 1220b, and the subject image 1220d can be treated as visible light images obtained when the white light irradiates the subject. The subject image 1220a includes a blood vessel image 1222a and a blood vessel image 1224a, the subject image 1220b includes a blood vessel image 1222b and a blood vessel image 1224b, and the subject image 1220d includes a blood vessel image 1222d and a blood vessel image 1224d.

The subject image 1220a, the subject image 1220b, and the subject image 1220d include surface images showing a physical surface in addition to the blood vessel images. The surface image acquiring section 214 generates a surface image of the subject at each first timing based on the light in the first wavelength region received by the first light receiving element 851 at the first timing, the light in the second wavelength region received by the second light receiving element 852 at the first timing, and the light in the third wavelength region received by the third light receiving element 853 at the first timing.

The object image acquiring section 210 generates a subject image 1220c, which includes a blood vessel image 1222c, a blood vessel image 1224c, and a blood vessel image 1226c, based on the light received by the light receiving elements at the second timings, represented by t1202. The subject image 1220c can be treated as an image of the subject captured using the luminescent light from the subject. The subject image 1220c is a target image of the blur correction process performed by the object image correcting section 220.

The subject image generating section 280 also generates a subject image 1230c, which includes the blood vessel images 1232c and 1234c, based on the amount of light received by the first light receiving element 851 at a first timing, e.g. t1201, and the amount of light received by the second light receiving element 852 and the third light receiving element 853 at a second timing, e.g. t1202. The subject image 1230c can be treated as a subject image acquired using visible light at a second timing, e.g. t1202.

In this way, the image processing section 140 generates a visible light subject image at the second timing, based on light in the second wavelength region received by the second light receiving element 852 at the second timing and light in the first wavelength region received by the first light receiving element 851 at the first timing. Accordingly, the image processing section 140 can generate a visible light image even at the timing at which the luminescent light image is captured. The output section 180 displays the visible light images 1220a, 1220b, 1230c, 1220d, etc. in series, thereby providing a video without missing frames.

If the subject 20 is a living organism having red blood like a person, the spatial frequency component of the red component in the visible light image is most likely smaller than the spatial frequencies of the green and blue components. Therefore, the amount of degradation of the video due to the red component frames being dropped is likely less than the amount of degradation due to green and blue component frames being dropped. Therefore, the choppy appearance of the video can be decreased more by dropping the red component than by dropping the green and blue components. Accordingly, the image processing system 10 can provide a visible light video without noticeable frame dropping.

As described above, the image processing system 10 can capture the subject image 1220c based on the luminescent light in the infra-red spectrum emitted by the subject 20 in response to the excitation light in the infra-red spectrum. Excitation light having a wavelength longer than visible light is more difficult to absorb than visible light, and therefore such excitation light penetrates more deeply, e.g. to a depth of approximately 1 cm, to cause the luminescent light to be emitted by the subject 20. Since the luminescent light has a longer wavelength than the excitation light, it is relatively easy for the luminescent light to reach the physical surface. Therefore, the image processing system 10 can achieve the subject image 1220c that includes the blood vessel image 1226d deep in the subject, which is not included in the visible light images 1220a, 1220b, and 1220d.

The output section 180 may generate a composite image obtained by combining the subject image 1220c with the subject image 1220b or the subject image 1220d that are captured at timings near the timing at which the subject image 1220c is captured. The output section 180 then outputs this composite image. The output section 180 may store the subject image 1220c in association with the subject image 1220b or the subject image 1220d.

The control section 105 cuts the light in the wavelength region of the excitation light and the light in the wavelength region of the luminescent light out of the light from the light emitting section 1010 at the timings at which the visible light images are captured. In this way, the image processing system 10 can provide an image of the physical surface for observation, without including the blood vessel images inside the subject in the visible light image.

Figure 13:
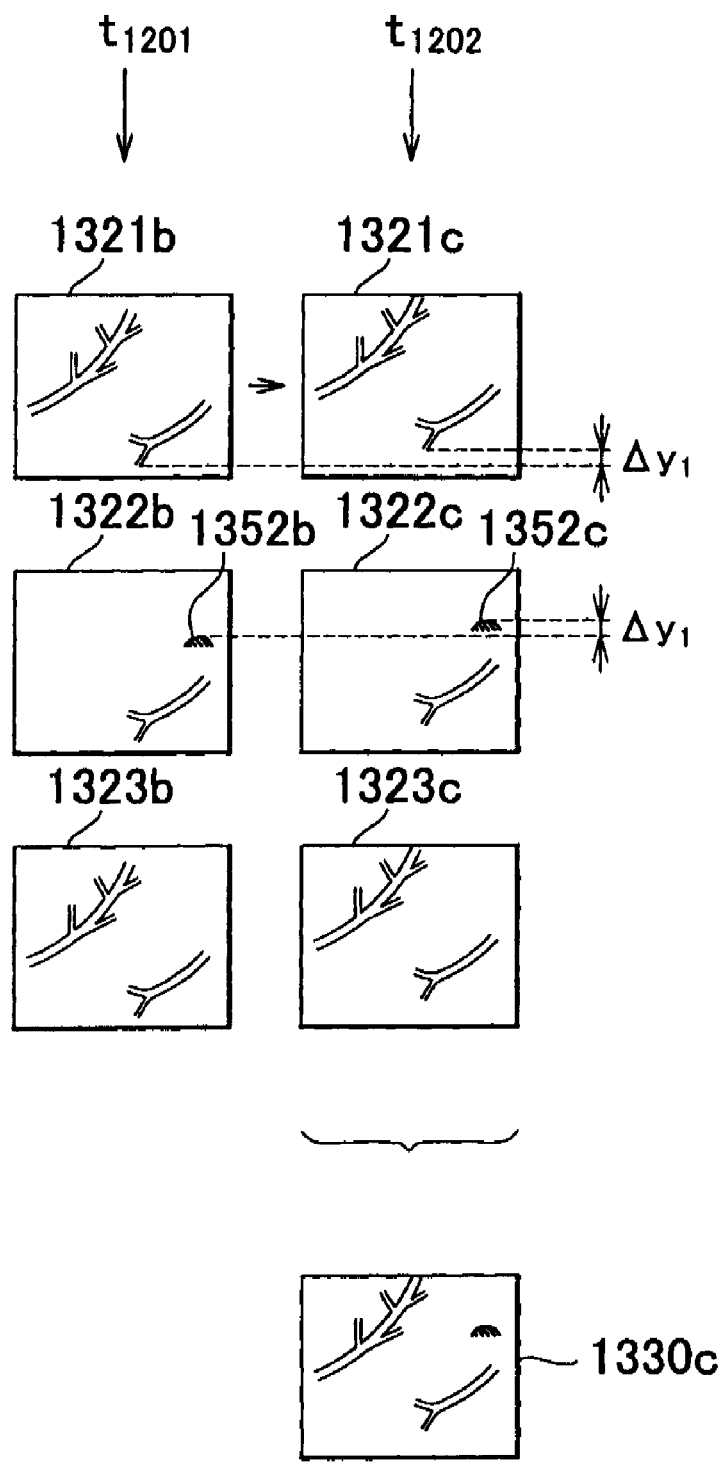
FIG. 13 shows the generation of a surface image in which the movement is corrected.

FIG. 13 shows the generation of a surface image in which the movement is corrected. For ease of explanation, FIG. 12 is used to describe an exemplary process of generating the visible light image 1230c by multiplexing an R signal corresponding to the amount of light received by the first light receiving element 851 at the time t1201 with a B signal and a G signal corresponding respectively to the amount of light received by the second light receiving element 852 and the third light emitting element 853 at the time t1202. In the following description, the movement of the tip 102 of the endoscope 100, the movement of the subject 20, and the like do not cause a change over time in the image. In this process, the R signal might be skewed in relation to other color signals in the visible light image due to movement of the tip 102 of the endoscope 100, movement of the subject 20, or the like.

The function and operation of the image processing section 140 for correcting the effect of movement on the visible light image, and in particular the operation of the subject image generating section 280 and the movement identifying section 270, are described in relation to FIGS. 13 and 14.

The movement identifying section 270 identifies movement of an object in an image, based on an image created by B signals at a plurality of timings. Here, the movement of an object refers to any movement that causes a change over time in the image, such as movement of the subject 20, movement of the tip 102 of the endoscope 100, or a change over time of the zoom of the image capturing section 110. The movement of the tip 102 of the endoscope 100 includes a change over time of the position of the tip 102 causing the position of the image captured by the image capturing section 110 to change over time, and a change over time of the orientation of the tip 102 that causes the direction in which the image capturing section 110 captures the image to change over time.

The movement identifying section 270 identifies the movement of an object based on the image of the B signal at the times t1201 and t1202. For example, the movement identifying section 270 identifies the movement of the object by matching the objects extracted from a plurality of images.

The subject image generating section 280 corrects the R signal at the time t1201 based on the identified movement, and generates the R signal that is expected for the time t1202. The subject image generating section 280 multiplexes the R signal generated through the above correction, the B signal at the time t1202, and the G signal at the time t1202, to generate the subject image at time t1202.

The image 1321b is the image of the R signal from the first light receiving element 851 at the time t1201. The image 1322b and the image 1322c are images of the B signal from the second light receiving element 852 at the times t1201 and t1202, respectively. The image 1323b and the image 1323c are images of the G signal from the third light receiving element 853 at the times t1201 and t1202, respectively.

Here, the movement identifying section 270 identifies the movement based on the content of the image 1322b and the image 1322c. More specifically, the movement identifying section 270 extracts objects from the image 1322b and the image 1322c that show the same subject. In the example of FIG. 13, the movement identifying section 270 extracts the objects 1352b and 1352c from the image 1322b and the image 1322c, respectively.

The movement identifying section 270 calculates the difference in position between the object 1352b and the object 1352c. In FIG. 13, for ease of explanation, the position difference exists in the y-direction of the image so that the movement identifying section 270 calculates a positional difference Δy1 indicating the positional difference between the object 1352b and the object 1352c.

The subject image generating section 280 generates the image 1321c by shifting the image 1321b in the y-direction by an amount corresponding to the calculated positional difference Δy1. The subject image generating section 280 generates the subject image 1330c by combining the image 1321c, the image 1322c, and the image 1323c. Here, combining the images includes a process for multiplexing the R signal showing the image 1321c, the B signal showing the image 1322c, and the G signal showing the image 1323c, with a prescribed weighting.

The above describes an example in which the movement is identified using the image 1322 of the B signal, but the movement can be identified in the same manner using the image 1323 of the G signal. The decision concerning which image's waveform the movement identifying section 270 uses to identify the movement can be decided based on the contrast of the captured image. For example, the movement identifying section 270 can prioritize the use of the image having the highest contrast for identifying the movement. If an object with a minute structure is used as the object for identifying the movement, i.e. it is clear that the object has a very fine surface structure, using the image of the B signal might enable more accurate movement identification. If an object with an uneven structure is used for identifying the movement, i.e. it is clear that the object has a bumpy surface structure, using the image of the G signal might enable more accurate movement identification.

The subject image generating section 280 may change the movement correction amount for each image region in the image of the R signal. For example, if the image capturing direction of the image capturing section 110 is perpendicular to the surface of the subject and the tip 102 of the endoscope 100 moves horizontally in relation to the surface of the subject, the movement amount of the object is the same in every image region. On the other hand, if the image capturing direction of the image capturing section 110 is not perpendicular to the surface of the subject, for example, the movement amount in image regions captured at positions further from the tip 102 might be smaller than the movement amount in image regions captured at positions closer to the tip 102.

In order to calculate the movement correction amount for each image region in the image of the R signal, the subject image generating section 280 can calculate the movement correction amount based on the position of an image region and a positional relationship between the surface of the subject and the image capturing section 110, if this positional relationship is known in advance or can be estimated. The subject image generating section 280 may calculate the movement correction amount for the image of the R signal based on a control value that manipulates the endoscope 100 to cause a change over time in the image. The control value may be a value that controls the position or orientation of the tip 102, a value that controls the zoom of the image capturing section 110, or the like.

As another example, the movement identifying section 270 may calculate the movement of the object in each image region. The subject image generating section 280 may calculate the movement correction amount for each image region in the image based on the movement of an object in each image region.

When identifying the movement in each image region, the movement identifying section 270 may determine which wavelength image is used to identify the movement in each image region. For example, the movement identifying section 270 calculates the contrast of each image region in each image. The movement identifying section 270 may then give priority to selecting the image of the wavelength for which the highest contrast was calculated and uses this image for the corresponding image region. The movement identifying section 270 uses the plurality of selected waveforms to identify the movement of the objects.

As described in relation to FIGS. 12 and 13, the movement identifying section 270 identifies the amount of movement of an object between an image at the first timing and an image at the second timing, based on the image resulting from the light in the second wavelength region received by the second light receiving element 852 at the first timing and the image resulting from the light in the second wavelength region received by the second light receiving element 852 at the second timing. The subject image generating section 280 generates the surface image at the second timing based on the light in the first wavelength region received by the first light receiving element 851 at the first timing, the light in the second wavelength region received by the second light receiving element 852 at the second timing, and the movement of the object.

FIG. 14 shows another example of the generation of a surface image in which the movement is corrected. In the examples in FIG. 14, the movement identifying section 270 identifies the movement using the image 1421a of the R signal obtained at the time t1200 and the image 1421b of the R signal obtained at the time t1201. In the same manner as the method described in relation to FIG. 13, the movement identifying section 270 extracts objects that indicate the same subject in the image 1421a and the image 1421b. In FIG. 14, the movement identifying section 270 extracts the object 1451a and the object 1451b from the image 1421a and the image 1421b, respectively.

The movement identifying section 270 calculates the positional difference between the object 1451a and the object 1451b. In FIG. 14, for ease of explanation, the position difference exists in the y-direction of the image so that the movement identifying section 270 calculates the positional difference Δy2 indicating the positional difference between the object 1451a and the object 1451b. In the same manner as described in relation to FIG. 13, the subject image generating section 280 generates the image 1421c by shifting the image 1421b in the y-direction by an amount corresponding to the calculated positional difference Δy2. The subject image generating section 280 generates the surface image 1430 by combining the image 1421c, the image 1422c, which is the G signal image from the third light receiving element 853 at the time t1202, and the image 1423c, which is the B signal image from the third light receiving element 853 at the time t1202.

The above example uses the image 1421a and the image 1421b to identify the movement, but the movement identifying section 270 may instead identify the movement using the image 1421b and the image of the R signal obtained at the time t1203. In this way, the movement identifying section 270 may identify the movement based on the images obtained at a plurality of timings before and after the time t1201, which is the timing at which the image of the R signal in which the movement is corrected is generated. If it is acceptable for the display of the visible light image to be somewhat delayed, the movement identifying section 270 can more accurately identify the movement by also using images at later timings.

As described in relation to FIG. 14 the movement identifying section 270 identifies the movement of the objects between images obtained at a plurality of timings, based on a plurality of images resulting from the light in the first wavelength region received by the first light receiving element 851 at a plurality of timings that include the first timings but not the second timing. The subject image generating section 280 generates the surface image at the second timing based on the light in the first wavelength region received by the first light receiving element 851 at the first timings, the light in the second wavelength region received by the second light receiving element 852 at the second timing, and the movement of the object.

FIGS. 13 and 14 are used to described examples of the movement identification processes in which the movement is identified using images captured by the movement identifying section 270 at the second timing, but the movement identifying section 270 may instead identify the movement using images captured at three or more timings. The movement identifying section 270 can select an image for identifying the movement for each image region, from among the images of the R signal in addition to the images of the B signal and the images of the G signal.

When performing the correction process described above on the subject image 1220c, the object image correcting section 220 can identify a correspondence between (i) the blood vessel image 1222c and the blood vessel image 1224c in the subject image 1220c and (ii) the blood vessel images 1222 and the blood vessel images 1224 in other subject images 1220, based on the movement identified by the movement identifying section 270.

The second light receiving element 852 and the third light receiving element 853 are sensitive to light in the wavelength of the luminescent light, and may receive the luminescent light from the subject at the second timings, represented by t1202. In this case, the spectral filter section 820 and the lens-side light cut filter 830 may allow the light in the wavelength region of the luminescent light to pass through.

In this case, the object image acquiring section 210 may generate the object image by performing a pixel adding process that adds together the image signals from among a first light receiving element 851, a second light receiving element 852, and a third light receiving element 853 that are near each other. Here, the image signal from each light receiving element is a signal indicating a charge amount corresponding to the amount of light received by the light receiving element. The signal indicating the charge amount may be an analog signal corresponding to the amount of light received by the light receiving element, or may be a digital signal obtained by AD converting the analog signal. The signal components of either type of signal can be amplified in the pixel adding process. The amount by which the pixel adding process amplifies the random noise is small in comparison to the amount by which the signal components are amplified. Therefore, the S/N ratio can be enhanced by the pixel adding process.

Using the same technique described in relation to FIGS. 13 and 14, the movement identifying section 270 may identify the movement using any one of the red component, the green component, or the blue component at a plurality of timings other than the second timings represented by t1202. The subject image generating section 280 can generate the visible light subject image that is expected to be captured at the second timings by correcting the visible light subject image obtained at timings other than the second timings.

In the above description, the light irradiating section 150 is configured to use a rotating filter and a single light source that can emit light that includes the wavelength region of the excitation light and the wavelength region of the visible light, but the light irradiating section 150 may instead emit the excitation light and the visible light at different times by controlling the light emission of a plurality of light emitting elements that emit light in a plurality of different wavelength regions. For example, semiconductor elements such as LEDs may be used as the light emitting elements that emit the light in the visible light wavelength region. Semiconductor elements such as semiconductor lasers may be used as the light emitting elements that emit light in the excitation light wavelength region. Furthermore, the light emitting elements may be fluorescent bodies that emit the luminescent light, i.e. fluorescent light, when excited.

The light emission control section 170 can cause the visible light and the light including the excitation light to be emitted at different times by controlling the emission intensity of each light emitting element at each timing. Here, "controlling the emission intensity of each light emitting element at each timing" refers to controlling a different combination of light emitting elements to emit light at each timing.

The light emitting elements may be provided on the tip 102 of the endoscope 100. The light emitting elements may emit light in response to electrical excitation or in response to optical excitation. If the light emitting elements emit light in response to optical excitation, the light irradiating section 150 may include the light emitting elements and an exciting section that emits light for exciting the light emitting elements. These light emitting elements may emit light in different spectrums according to the wavelength of the light for excitation. In this case, the light emission control section 170 controls the wavelength of the light for excitation emitted by the exciting section at each timing to control the spectrum of the irradiation light. Each light emitting element may emit light in a different spectrum in response to the same light for excitation. The light passing through the light emitting elements, from the light for excitation, may irradiate the subject as the irradiation light.

The above describes a configuration in which the spectral filter section 820 is provided on the light receiving side in the image capturing section 110, but the spectral filter section 820 need not be provided to the image capturing section 110. In this case, the light irradiating section 150 may radiate the light in the red wavelength region, the light in the green wavelength region, the light in the blue wavelength region, and the light in the wavelength region of the excitation light at separate timings. By multiplexing the signals from a plurality of light receiving elements when the visible light is radiated, the surface image acquiring section 214 can generate the visible light subject image. The object image acquiring section 210 can generate the luminescent light subject image using the signals from the light receiving elements at the timing when the excitation light is radiated.

The configuration of the light irradiating section 150 that enables the light in the red wavelength region, the light in the green wavelength region, the light in the blue wavelength region, and the light in the wavelength region of the excitation light to be radiated at separate timings includes (i) one or more light sources that can emit light that includes the wavelength regions of the excitation light and visible light and (ii) a rotating filter having a plurality of filter portions that each selectively allow a majority of light in a certain wavelength region to pass through.

With the configuration in which the light in each wavelength region is radiated at a separate timing as well, the movement identifying section 270 can identify the movement using one or more of the image signals of each color at the plurality of timings, as described in relation to FIGS. 13 and 14. The subject image generating section 280 can generate an R signal image that is expected to be obtained at the timing at which the light in the red wavelength region is not radiated, based on the movement and the R signal image at the timing at which the light in the red wavelength region is radiated, for example. In the same way, the subject image generating section 280 can generate the G signal image at the timing at which the light in the green wavelength region is not radiated and the B signal image at the timing at which the light in the blue wavelength region is not radiated. In this way, the subject image generating section 280 can generate the visible light image at each timing.

Figure 15:
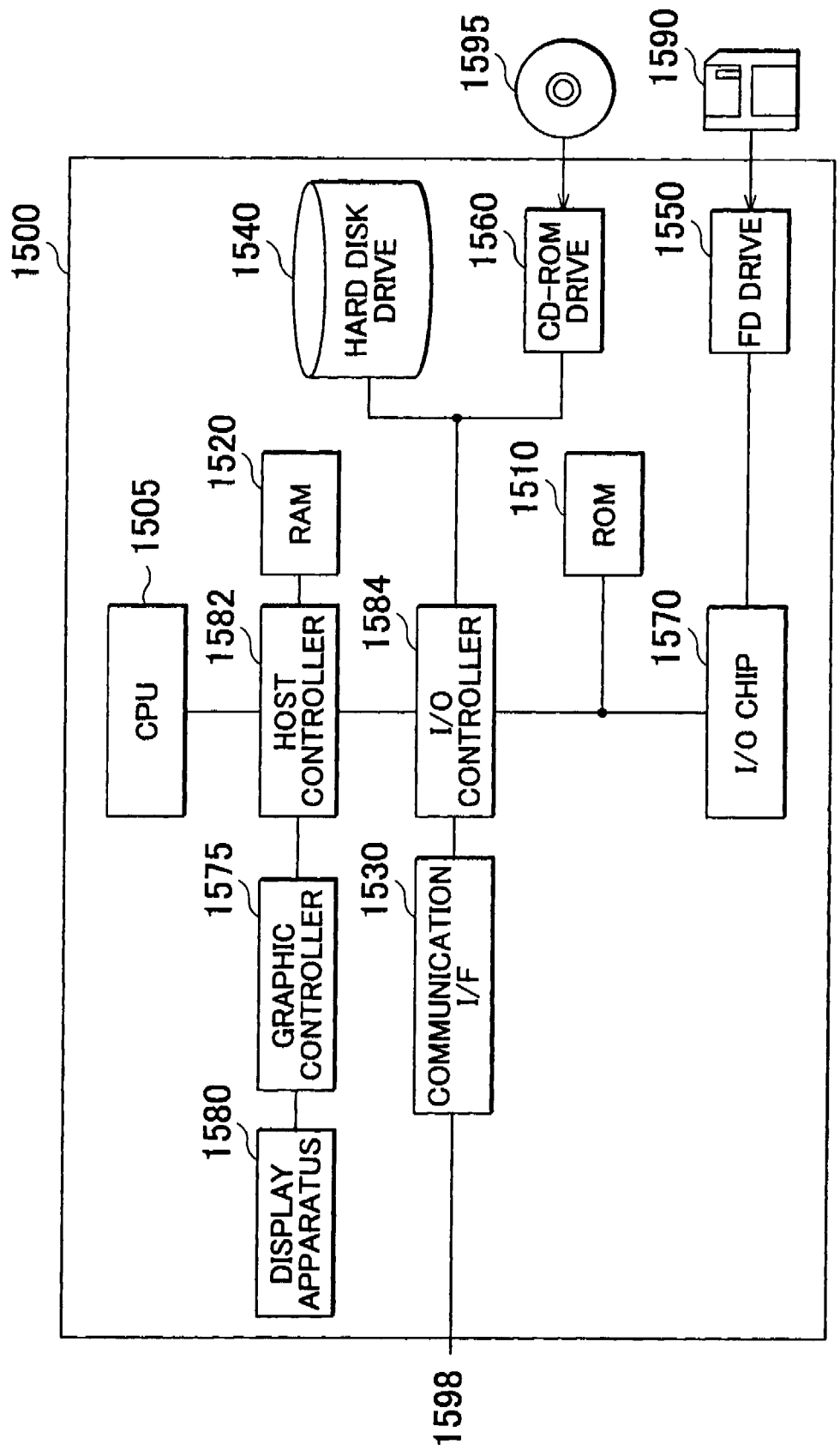
FIG. 15 shows an exemplary hardware configuration of a computer 1500 functioning as the image processing system 10.

FIG. 15 shows an exemplary hardware configuration of a computer 1500 functioning as the image processing system 10. The image processing system 10 according to the present embodiment is provided with a CPU peripheral section that includes a CPU 1505, a RAM 11120, a graphic controller 1575, and a display apparatus 1580 connected to each other by a host controller 1582; an input/output section that includes a communication interface 1530, a hard disk drive 1540, and a CD-ROM drive 1560, all of which are connected to the host controller 1582 by an input/output controller 1584; and a legacy input/output section that includes a ROM 11110, a flexible disk drive 1550, and an input/output chip 1570, all of which are connected to the input/output controller 1584.

The host controller 1582 is connected to the RAM 11120 and is also connected to the CPU 1505 and graphic controller 1575 accessing the RAM 11120 at a high transfer rate. The CPU 1505 operates to control each section based on programs stored in the ROM 11110 and the RAM 11120. The graphic controller 1575 acquires image data generated by the CPU 1505 or the like on a frame buffer disposed inside the RAM 11120 and displays the image data in the display apparatus 1580. In addition, the graphic controller 1575 may internally include the frame buffer storing the image data generated by the CPU 1505 or the like.

The input/output controller 1584 connects the hard disk drive 1540, the communication interface 1530 serving as a relatively high speed input/output apparatus, and the CD-ROM drive 1560 to the host controller 1582. The communication interface 1530 communicates with other apparatuses via the network. The hard disk drive 1540 stores the programs used by the CPU 1505 in the image processing system 10. The CD-ROM drive 1560 reads the programs and data from a CD-ROM 1595 and provides the read information to the hard disk drive 1540 via the RAM 11120.

Furthermore, the input/output controller 1584 is connected to the ROM 11110, and is also connected to the flexible disk drive 1550 and the input/output chip 1570 serving as a relatively high speed input/output apparatus. The ROM 11110 stores a boot program performed when the image processing system 10 starts up, a program relying on the hardware of the image processing system 10, and the like. The flexible disk drive 1550 reads programs or data from a flexible disk 1590 and supplies the read information to the hard disk drive 1540 and via the RAM 11120. The input/output chip 1570 connects the flexible disk drive 1550 to each of the input/output apparatuses via, for example, a parallel port, a serial port, a keyboard port, a mouse port, or the like.

The programs provided to the hard disk drive 1540 via the RAM 11120 are stored on a recording medium such as the flexible disk 1590, the CD-ROM 1595, or an IC card and are provided by the user. The programs are read from the recording medium, installed on the hard disk drive 1540 in the image processing system 10 via the RAM 11120, and are performed by the CPU 1505. The programs installed in the image processing system 10 and executed by the image processing system 10 affect the CPU 1505 to cause the image processing system 10 to function as the image capturing section 110, the image processing section 140, the output section 180, the control section 105, the light irradiating section 150, and the like described in relation to FIGS. 1 to 14.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

What is claimed is:

1. An image processing system, comprising:
    a depth calculating section that calculates a depth of a first object from a surface of a body, the first object existing inside the body;
    a light receiving section that receives light from the first object; and
    a substance amount calculating section that calculates an amount of a substance, which generates the light received by the light receiving section, inside the first object based on the depth of the first object calculated by the depth calculating section and an amount of light received by the light receiving section.

2. The image processing system according to claim 1, wherein
    the light receiving section receives light from a second object containing an amount of the substance substantially equal to the amount of the substance contained in the first object, and
    the depth calculating section calculates the depth of the second object based on the amount of the substance calculated by the substance amount calculating section and an amount of light from the second object received by the light receiving section.

3. The image processing system according to claim 2, wherein
    the light receiving section receives light in a plurality of waveform regions from the second object, and
    the depth calculating section calculates the depth of the second object based on the amount of the substance calculated by the substance amount calculating section and an amount of light in each of the plurality of wavelength regions from the second object received by the light receiving section.

4. The image processing system according to claim 3, wherein
    when the depth of the first object calculated by the depth calculating section is less than a preset value, the substance amount calculating section calculates the amount of the substance in the first object based on the depth of the first object calculated by the depth calculating section and the amount of light from the first object received by the light receiving section.

5. The image processing system according to any one of claim 3 or claim 4, wherein
    the depth calculating section calculates the depth of the second object based on the amount of the substance calculated by the substance amount calculating section and the amount of light in each of the plurality of waveform regions from the second object received by the light receiving section, where the second object is at a position deeper from the surface than the first object.

6. The image processing system according to claim 2, wherein
the light receiving section receives light from the first object that includes light emitted by a luminescent substance inside the first object, and
the substance amount calculating section calculates an amount of the luminescent substance inside the first object based on the depth of the first object calculated by the depth calculating section and the amount of the light emitted by the luminescent substance that is received by the light receiving section.

7. The image processing system according to claim 6, wherein
the light receiving section receives light in a plurality of wavelength regions including light emitted by the luminescent substance inside the second object positioned deeper from the surface than the first object, and
the depth calculating section calculates the depth of the second object based on the amount of the luminescent substance calculated by the substance amount calculating section and the amount of light in each of the plurality of wavelength regions from the second object received by the light receiving section.

8. The image processing system according to claim 7, further comprising a depth information storing section that stores the depth of the first object from the surface of the body in association with the amount of the luminescent substance inside the first object and the amount of light in each of the plurality of wavelength regions from the first object, wherein
the depth calculating section calculates the depth of the second object based on the depth stored in the depth information storing section, the amount of the luminescent substance calculated by the substance amount calculating section, and the amount of the light in each of the plurality of wavelength region from the second object received by the light receiving section.

9. The image processing system according to claim 6, wherein
the light receiving section receives light in the plurality of wavelength regions including light emitted by the luminescent substance inside the first object, the luminescent substance being injected into the first object, and
the substance amount calculating section calculates the amount of the luminescent substance injected into the first object.

10. The image processing system according to claim 9, further comprising:
a substance amount storing section that stores thereon the amount of the luminescent substance inside the first object calculated by the substance amount calculating section; and
a substance amount updating section that, on a condition that a new amount of the luminescent substance calculated by the substance amount calculating section differs from the amount of the luminescent substance stored on the substance amount storing section by an amount greater than or equal to a preset value, updates the amount of the luminescent substance stored on the substance amount storing section to be the new amount of the luminescent substance calculated by the substance amount calculating section.

11. The image processing system according to claim 10, wherein the light receiving section receives light in a plurality of wavelength regions from the first object, and
the depth calculating section calculates the depth of the first object from the surface based on the amount of light in each of the plurality of wavelength regions received by the light receiving section.

12. The image processing system according to claim 2, further comprising:
an object image acquiring section that acquires an object image, which is an image of the second object captured through the surface; and
an object image correcting section that corrects the object image acquired by the object image acquiring section, based on the depth of the second object calculated by the depth calculating section.

13. The image processing system according to claim 12, wherein
the object image correcting section corrects spread of the object image caused by scattering of the light from the second object between the second object and the surface, based on the depth of the second object calculated by the depth calculating section.

14. The image processing system according to claim 13, further comprising a correction table that stores a correction value for correcting the spread of the object image in association with the depth of the second object from the surface, wherein
the object image correcting section corrects the spread of the object image based on the correction value and the depth calculated by the depth calculating section.

15. The image processing system according to claim 12, further comprising a display control section that controls display of the object image corrected by the object image correcting section, according to the depth.

16. The image processing system according to claim 15, wherein
the display control section changes a brightness of an image of the first object in the object image corrected by the object image correcting section, according to the depth.

17. An image processing method, comprising:
calculating a depth of a first object from a surface of a body, the first object existing inside the body;
receiving light from the first object; and
calculating an amount of a substance, which generates the received light, inside the first object based on the calculated depth of the first object and an amount of received light.

18. A computer readable medium storing thereon a program for use with an image processing system, when executed the program causing the image processing system to function as:
a depth calculating section that calculates a depth of a first object from a surface of a body, the first object existing inside the body;
a light receiving section that receives light from the first object; and
a substance amount calculating section that calculates an amount of a substance, which generates the light received by the light receiving section, inside the first object based on the depth of the first object calculated by the depth calculating section and an amount of light received by the light receiving section.

* * * * *